United States Patent
Udipi et al.

(10) Patent No.: US 9,687,368 B2
(45) Date of Patent: *Jun. 27, 2017

(54) BIOCOMPATIBLE CONTROLLED RELEASE COATINGS FOR MEDICAL DEVICES AND RELATED METHODS

(75) Inventors: Kishore Udipi, Santa Rosa, CA (US); Peiwen Cheng, Santa Rosa, CA (US); Shalaby W. Shalaby, Anderson, SC (US); Todd Campbell, Petaluma, CA (US); Su Ping Lyu, Maple Grove, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1305 days.

This patent is subject to a terminal disclaimer.

(21) Appl. No.: 10/595,095

(22) PCT Filed: Aug. 12, 2004

(86) PCT No.: PCT/US2004/026516
§ 371 (c)(1),
(2), (4) Date: Feb. 9, 2006

(87) PCT Pub. No.: WO2005/016396
PCT Pub. Date: Feb. 24, 2005

(65) Prior Publication Data
US 2006/0275340 A1    Dec. 7, 2006

Related U.S. Application Data

(60) Provisional application No. 60/495,143, filed on Aug. 13, 2003.

(51) Int. Cl.
| | | |
|---|---|---|
| *A61K 31/4745* | (2006.01) | |
| *A61F 2/02* | (2006.01) | |
| *A61L 31/10* | (2006.01) | |
| *A61F 2/06* | (2013.01) | |
| *A61L 31/16* | (2006.01) | |
| *A61F 2/91* | (2013.01) | |
| *A61F 2/915* | (2013.01) | |
| *A61L 31/06* | (2006.01) | |

(52) U.S. Cl.
CPC ............... *A61F 2/91* (2013.01); *A61F 2/915* (2013.01); *A61L 31/06* (2013.01); *A61L 31/10* (2013.01); *A61L 31/16* (2013.01); *A61F 2002/91541* (2013.01); *A61F 2250/0067* (2013.01); *A61L 2300/406* (2013.01); *A61L 2300/602* (2013.01)

(58) Field of Classification Search
None
See application file for complete search history.

(56) References Cited

U.S. PATENT DOCUMENTS

| | | |
|---|---|---|
| 5,094,876 A | 3/1992 | Goldberg et al. |
| 5,342,628 A | 8/1994 | Picha |
| 6,015,815 A | 1/2000 | Mollison |
| 6,258,121 B1 | 7/2001 | Yang et al. |
| 6,329,386 B1 | 12/2001 | Mollison |
| 6,344,035 B1 | 2/2002 | Chudzik et al. |
| 6,756,449 B2 | 6/2004 | Benz et al. |
| 6,776,796 B2 | 8/2004 | Llanos et al. |
| 7,018,405 B2 | 3/2006 | Sirhan et al. |
| 7,041,308 B2 | 5/2006 | Shalaby et al. |
| 7,815,927 B2 | 10/2010 | Cheng et al. |
| 2002/0042645 A1* | 4/2002 | Shannon .................. 623/1.13 |
| 2002/0082677 A1* | 6/2002 | Sirhan et al. ............. 623/1.15 |
| 2002/0142039 A1* | 10/2002 | Claude .............. A61K 9/0024 424/486 |
| 2002/0188037 A1 | 12/2002 | Chudzik et al. |
| 2003/0129215 A1 | 7/2003 | Mollison et al. |
| 2003/0162905 A1* | 8/2003 | Benz et al. .................. 525/294 |
| 2003/0170287 A1 | 9/2003 | Prescott |
| 2003/0199964 A1* | 10/2003 | Shalaby et al. ............. 623/1.11 |
| 2004/0033251 A1 | 2/2004 | Sparer et al. |
| 2004/0047911 A1* | 3/2004 | Lyu et al. .................... 424/487 |
| 2004/0086569 A1 | 5/2004 | Sparer et al. |
| 2004/0115273 A1 | 6/2004 | Sparer et al. |
| 2004/0127978 A1 | 7/2004 | Sparer et al. |
| 2005/0064005 A1 | 3/2005 | Dinh et al. |
| 2005/0064038 A1 | 3/2005 | Dinh et al. |
| 2005/0084515 A1 | 4/2005 | Udipi et al. |
| 2006/0099235 A1 | 5/2006 | Blakstvedt et al. |
| 2006/0275340 A1 | 12/2006 | Udipi et al. |
| 2007/0225785 A1 | 9/2007 | Park et al. |

(Continued)

FOREIGN PATENT DOCUMENTS

| | | |
|---|---|---|
| EP | 0544144 | 6/1993 |
| WO | PCT/US2004/26515 | 8/2003 |

(Continued)

OTHER PUBLICATIONS

Van Krevelen, "Properties of Polymers," 1990, Elsevier, 3rd Edition, Chapter 7, pp. 189-225.*
Hezi-Yamit et al., "Impact of polymer hydrophilicity on biocompatibility: Implication for DES polymer design," *J. Biomed. Mater. Res,* 2009; 90A:133-141.
Meredith et al., "The next-generation Endeavor™ Resolute™ stent: 4-month clinical and angiographic results from the Endeavor™ Resolute™ first-in-man trial," *EuroIntervention,* 2007; 3:50-53.
"Resolute All Comers: International Multicentre DES Clinical Trial; 12-Month Results Summary: Resolute DES Matches Xience V DES," Medtronic, Inc. © 2010; 20 pgs.
Serruys et al., "Comparison of Zotarolimus-Eluting and Everolimus-Eluting Coronary Stents," *N Engl J Med,* 2010; 363:136-146.

(Continued)

*Primary Examiner* — Brian Gulledge

(57) ABSTRACT

Biocompatible coatings for medical devices are disclosed. Specifically, polymer coatings designed to control the release of bioactive agents from medical devices in vivo are disclosed wherein the solubility parameters of polymers and drugs are closely matched to control elute rate profiles. The present application also discloses providing vascular stents with controlled release coatings and related methods for making these coatings.

51 Claims, 4 Drawing Sheets

(56) References Cited

U.S. PATENT DOCUMENTS

2008/0220046 A1  9/2008  Cheng et al.
2009/0043378 A1  2/2009  Cheng et al.
2010/0094407 A1  4/2010  Vasquez et al.

FOREIGN PATENT DOCUMENTS

WO  WO 2004/014447  2/2004
WO  WO 2005/016396  2/2005

OTHER PUBLICATIONS

Udipi et al., "Development of a novel biocompatible polymer system for extended drug release in a next-generation drug-eluting stent," *J. Biomed. Mater. Res.*, 2008; 85A:1064-1071.

* cited by examiner

BIOCOMPATIBLE CONTROLLED RELEASE COATINGS FOR MEDICAL DEVICES AND RELATED METHODS

RELATED APPLICATION

This application is a national stage entry under 35 U.S.C. §371 of PCT/US2004/026516, filed Aug. 12, 2004, which claims priority to U.S. Provisional Patent Application Ser. No. 60/495,143, filed Aug. 13, 2003, and is a continuation-in-part of U.S. patent application Ser. No. 10/393,880 filed Mar. 20, 2003 (issued as U.S. Pat. No. 7,041,308 on Mar. 9, 2006).

FIELD OF THE INVENTION

This invention relates generally to biocompatible coatings for medical devices. More specifically, the present invention relates to polymer coatings designed to control the release of bioactive agents from a medical device. Even more specifically the present invention relates to providing vascular stents with controlled release coatings and related methods for making these coatings.

BACKGROUND OF THE INVENTION

Medical devices are used for myriad purposes on and throughout an animal's body. They can be simple ex vivo devices such as adhesive bandages, canes, walkers and contact lenses or complex implantable devices including pace makers, heart valves, vascular stents, catheters and vascular grafts. Implantable medical devices must be biocompatible to prevent inducing life threatening adverse physiological responses between the implant recipient and device.

Recently, highly biocompatible polymers have been formulated to provide implantable medical devices with coatings. These coatings not only increase an implant's tissue compatibility but can also function as bioactive agent reservoirs. However, designing polymer coatings for medical devices have proven problematic. All medical device coatings must be non-toxic, durable and adhere well to device surfaces. Additionally, when the medical device comes into intimate contact with unprotected tissues such as blood and internal organs it must also be biocompatible. Furthermore, if the medical device is designed to be pliable either in operation or deployment, the coating must resist cracking, fracture and delamination.

Moreover, medical devices intended to act as bioactive agent (drug) reservoirs must not only be biocompatible, structurally stable and resistant to delamination, but also chemically compatible with the drug to be deployed. Furthermore, if the reservoir is also intended to control the drug's release rate into adjacent tissue the polymer used must possess other highly specialized properties as well.

Presently, designing a biocompatible polymer coating having the desired physical and chemical properties has been largely a process of trial and error. Material scientists skilled in polymer chemistry make a preliminary polymer selection based largely on educated guesses. Next a series of experiments designed to establish the new coating composition's performance characteristics are performed and the results compared to an idealized model. However, very few potential polymer compositions will possess all of the desired properties required for a medical device controlled release coating. Consequently, present controlled release coating development processes are tedious, time consuming and seldom result in an optimized medical device coating having the combination of biocompatibility, ductility, surface adhesiveness and drug-polymer solubility.

Drug-polymer physical chemistry and the physical characteristics of the coating itself, such as coating thickness, are the two most important factors in determining a polymer matrix's drug elusion profile. Highly compatible drug-polymer combinations usually result in more even elution rates and are therefore preferable for most in vivo applications. Polymer-drug compatibility is a function of drug-polymer miscibility. The degree of miscibility, or compatibility, between a drug and a polymer carrier can be ascertained by comparing their relative solubility parameters. However, as will be more fully developed below, balancing drug elution rates with biocompatibility, ductility and adhesiveness requires more than merely matching a single polymer with a drug based on their total solubility parameters alone.

Therefore, it is an object of the present invention to provide medical device controlled release coatings made using a process that reduces trial and error and results in drug delivery systems having ideal physical and chemical properties.

Specifically, it is an object of the present invention to provide medical device coating systems that are flexible, do not delaminate from the device's surface, are highly biocompatible and provide for the controlled release of bioactive agents.

SUMMARY OF THE INVENTION

The present invention generally provides methods and related polymer compositions useful for controlling drug release in vivo. Specifically, these methods and related polymer compostions are useful in providing controlled release coatings for medical devices. In one embodiment the medical device is subjected to compressive, expansive or flexion forces during use and/or deployment.

The controlled release polymer coatings of the present invention are intended for use inside an animal's body where the device will remain in intimate contact with body tissues for a prolonged time period. Therefore, in one embodiment of the present invention, the coating compostions of the present invention must be biocompatible, non-thrombogenic, non-inflammatory, lubricious and non-bioerodable.

In another embodiment of the present invention the controlled release polymer coatings must be ductile and possess glass transition points (Tg) sufficient to maintain elasticity/ductility at and near body temperature. In another embodiment of the present invention the controlled release polymer coatings have a Tg whereby elasticity/ductility is maintained from approximately −20° C. to 50° C. and above.

In one embodiment of the present invention the controlled release polymer coatings are compatible polymer blends or terpolymers. The novel compatible polymer blends and terpolymers made in accordance with the teachings of the present invention provide biocompatible, non-thrombogenic, non-bioerodable, elasticity/ductile coatings for implantable medical devices. These novel medical device coatings also provide for localized, controlled release drug delivery.

The novel compatible polymeric controlled release coatings of the present invention are prepared using novel methods of carefully matching specific polymer Tg and solubility parameters with drug solubility. In one embodiment of the present invention Hansen solubility parameters (dispersion force [$\delta_D$], polar force [$\delta_P$], and hydrogen bonding force [$\delta_H$]) are used to design polymer compositions having a total solubility parameter ($\delta_T$) within a defined range for the selected drug, or drug combination and a Tg appropriate for the compatible polymeric controlled release coating's intended use.

In one embodiment of the present invention the compatible polymeric controlled release coatings of the present invention are a blend of copolymers or a blend of copolymers and homopolymers.

In another embodiment of the present invention the polymer blend is a bipolymer blended with a second bipolymer or homopolymer.

In one embodiment of the present invention the polymer composition is a terpolymer.

In another embodiment of the present invention the polymer composition is a terpolymer blended with a second polymer composition selected from the non-limiting group of terpolymers, bipolymers and homopolymers.

In another embodiment of the present invention the drug or drug combination has a $\delta_T$ approximately equal to the polymer composition's $\delta_T$.

In another embodiment methods are provided for selecting individual polymers having Hansen solubility parameters optimized to achieve predetermined polymer composition performance characteristics including biocompatibility, elasticity/ductility, erosion resistance, and drug release profile thus forming the compatible controlled release coatings of the present invention.

Another embodiment of the present invention includes methods for using Hansen solubility parameters to provide a compatible polymeric controlled release coatings for a medical device wherein the coating comprises a terpolymer having a drug elusion profile and Tg suitable for long term deployment in a hemodynamic environment.

In one embodiment of the present invention the polymer compositions have $\delta_T$ values in the range of approximately 15 to 25 $\delta$ ($J^{1/2}/cm^{3/2}$).

It is an objective of the present invention to provide methods for making compatible polymeric controlled release coatings having target diffusivities as well as the compatible polymeric controlled release coatings themselves. The target diffusivities being tunable using copolymers and terpolymers having solubility parameters closely matched to the solubility parameter of the bioactive agent. One method for achieving a target diffusivity in accordance with the teachings of the present invention is to blend homopolymers and/or copolymers such that a $\delta_T$ is within approximately 10 $J^{1/2}/cm^{3/2}$ of the bioactive agent.

For example, in one embodiment of the present invention at least two polymers are selected having Hansen solubility parameters and Tg values balanced such that the resulting polymer composition is compatible with the bioactive agent. In this embodiment particular attention is given to compensating for undesirable polymer physical qualities present in otherwise desirable polymers. The physical factors to be compensated to include Hansen solubility parameters selected from the group consisting of $\delta_D$, $\delta_P$ and $\delta_H$. The resulting compatible polymer blend possesses net physical-chemical properties ideal for the bioactive agent to be released and the release kinetics desired. As used herein this process, and others described below are collectively referred to as "tuning" the polymer composition and the resulting compatible polymeric controlled release coatings are referred to herein as "tunable."

Additional tunable compatible polymeric controlled release coatings made in accordance with the teachings of the present invention include, but are not limited to hydrophobic or hydrophilic bioactive agents and a compatible polymer blend comprising at least two polymers, each with at least one solubility parameter, wherein: the difference between the solubility parameter of the bioactive agent and at least one solubility parameter of at least one of the polymers is no greater than about 10 $J^{1/2}/cm^{3/2}$, and/or the difference between at least one solubility parameter of each of at least two polymers is no greater than about 5 $J^{1/2}/cm^{3/2}$; at least one polymer has an bioactive agent diffusivity higher than the target diffusivity and at least one polymer has an bioactive agent diffusivity lower than the target diffusivity; the molar average solubility parameter of the blend is no greater than 25 $J^{1/2}/cm^{3/2}$; and the swellability of the blend is no greater than 10% by volume.

Another embodiment of the present invention include a method for making tunable compatible polymeric controlled release coatings. The method comprises providing a bioactive agent having a molecular weight no greater than about 1200 g/mol; selecting at least two polymers, wherein: the difference between the solubility parameter of the bioactive agent and at least one solubility parameter of each of the polymers is no greater than about 10 $J^{1/2}/cm^{3/2}$, and/or the difference between at least one solubility parameter of each of the at least two polymers is no greater than about 5 $J^{1/2}/cm^{3/2}$; and the difference between at least one Tg of each of the at least two polymers is sufficient to include the target diffusivity; combining the at least two polymers to form a compatible polymer blend; and combining the compatible polymer blend with the bioactive agent to form an bioactive agent delivery system having the preselected dissolution time through a preselected critical dimension of the compatible polymer blend.

A further method for making tunable compatible polymeric controlled release coatings in accordance with the present invention include providing a bioactive agent having a molecular weight greater than about 1200 g/mol; selecting at least two polymers, wherein: the difference between the solubility parameter of the bioactive agent and at least one solubility parameter of each of the polymers is no greater than about 10 $J^{1/2}/cm^{3/2}$, and/or the difference between at least one solubility parameter of each of the at least two polymers is no greater than about 5 $J^{1/2}/cm^{3/2}$; and the difference between the swellabilities of the at least two polymers is sufficient to include the target diffusivity; combining the at least two polymers to form a compatible polymer blend; and combining the compatible polymer blend with the bioactive agent to form an bioactive agent delivery system having the preselected dissolution time through a preselected critical dimension of the compatible polymer blend.

The compatible polymeric controlled release coatings of the present invention are used to coat drug eluting medical devices. In one embodiment of the present invention the medical device is selected from the non-limiting group consisting of vascular stents, vascular stent grafts, urethral stents, bile duct stents, catheters, inflation catheters, injection catheters, guide wires, pace maker leads, ventricular assist devices, and prosthetic heart valves.

In another embodiment the drug, or drug combination eluted from the compatible controlled release coatings of the present invention include, but are not limited to bioactive agents such as anti-proliferative compounds, cytostatic compounds, cytotoxic compounds, anti-inflammatory compounds, analgesics, antibiotics, protease inhibitors, tyrosine kinase inhibitors, aldosterone inhibitors, bisphosphonates, statins, nucleic acids, polypeptides, proteins and gene delivery vectors including recombinant micro-organisms, liposomes, and the like.

In another embodiment of the present invention the coated medical device is intended to treat physiological and anatomical pathologies in a hemodynamic region of an animal such as the cardiovascular system, the respiratory system, the neurological system and the peripheral vascular system. In one embodiment of the present invention the medical device is a vascular stent used to treat, inhibit, palliate or prevent vascular occlusions and vulnerable plaque. In another embodiment of the present invention the medical device is a vascular graft used to treat, inhibit, palliate or prevent aneurysms.

In one particular non-limiting example the present invention includes a vascular stent having a compatible controlled release coating made in accordance with the present invention. The vascular stent is used to treat an existing vascular occlusion in at least one coronary artery. A terpolymer-based coating mediates the controlled release of a bioactive compound that inhibits restenosis or stabilized vulnerable plaque. When the stent is used to inhibit restenosis, the bioactive compound is an anti-proliferative including, but not limited to, macrolide antibiotics including FKBP 12 binding compounds, estrogens, chaperone inhibitors, protein-tyrosine kinase inhibitors, peroxisome proliferator-activated receptor gamma ligands (PPARγ), hypothemycin, nitric oxide, anti-sense nucleotides and transforming nucleic acids. Stents for stabilizing vulnerable plaque may deploy any of the aforementioned bioactive compounds alone or in combination with anti-inflammatory compounds and/or protease inhibitors, specifically matrix metalloproteinase inhibitors (MMPIs) such as tetracycline-class antibiotics.

The compatible polymeric controlled release coatings made in accordance with the teachings of the present invention can be made form any combination of polymers that combine to form novel polymer compositions that exhibit the combined properties of biocompatibility, high elasticity/ductility, resistance to erosion, elasticity, and controlled drug release. Suitable non-limiting exemplary monomers include hydroxy alkyl methacrylate, N-vinyl pyrrolidinone, alkyl methacrylate, vinyl alcohols, acrylic acids, acrylamides, ethylene, vinyl acetate, ethylene glycol di(meth)acrylate, methacrylic acid and co-polymers thereof.

DEFINITION OF TERMS

Figure 1:
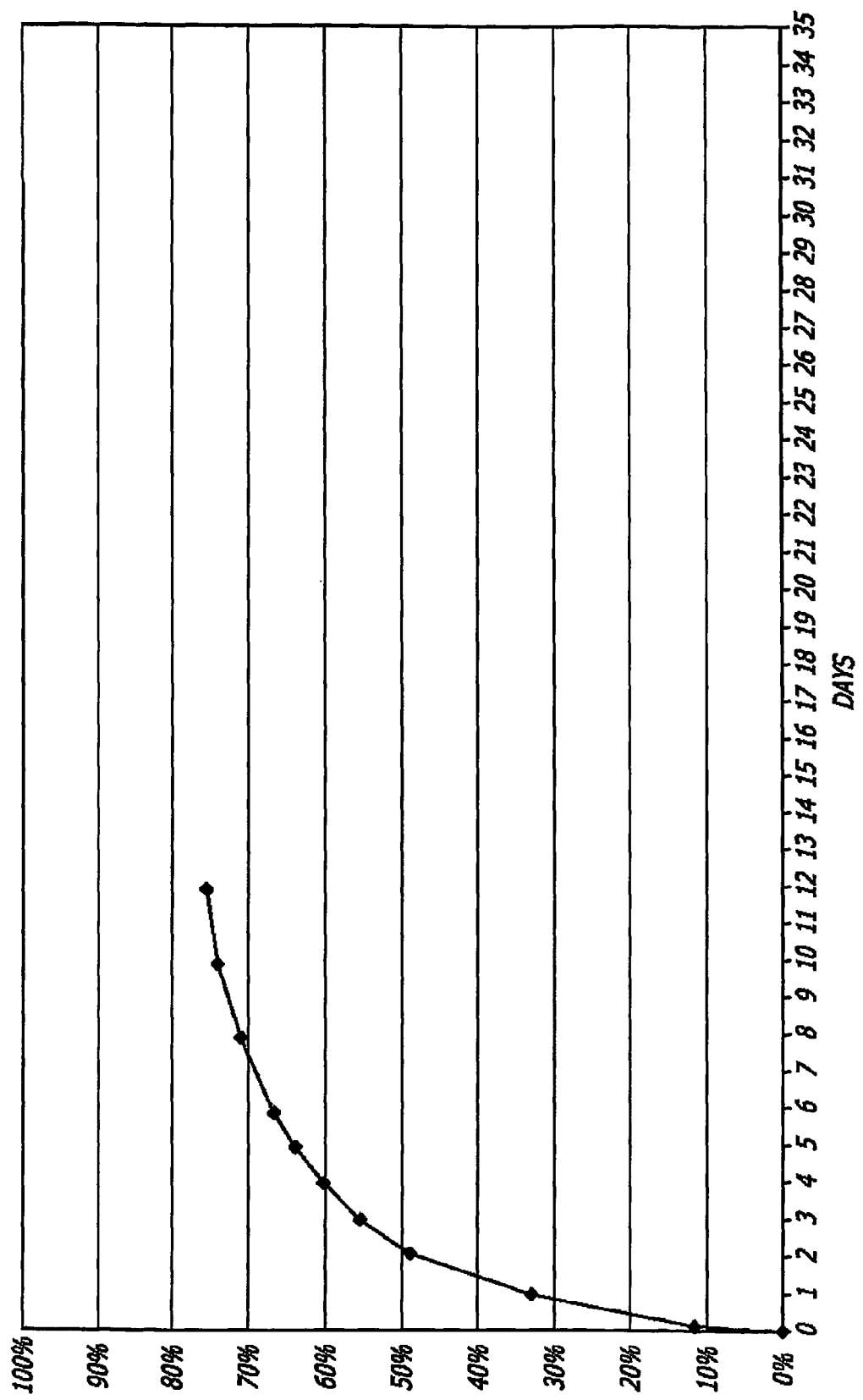
FIG. 1 graphically depicts idealized first-order kinetics associated with drug release from a polymer coating.

Prior to setting forth the invention, it may be helpful to an understanding thereof to set forth definitions of certain terms that will be used hereinafter:

Animal: As used herein "animal" shall include mammals, fish, reptiles and birds. Mammals include, but are not limited to, primates, including humans, dogs, cats, goats, sheep, rabbits, pigs, horses and cows.

Biocompatible: As used herein "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis.

Bioactive agent: As used herein "bioactive agent" shall included anti-proliferative compounds, cytostatic compounds, toxic compounds, anti-inflammatory compounds, analgesics, antibiotics, protease inhibitors, statins, nucleic acids, polypeptides, and delivery vectors including recombinant micro-organisms, liposomes, the like (see Drugs below).

Controlled release: As used herein "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of drug may be desirable followed by a more gradual release thereafter. The release rate may be steady state (commonly referred to as "timed release" or zero order kinetics), that is the drug is released in even amounts over a predetermined time (with or without an initial burst phase) or may be a gradient release. A gradient release implies that the concentration of drug released from the device surface changes over time.

Compatible: As used herein "compatible" refers to a composition possess the optimum, or near optimum combination of physical, chemical, biological and drug release kinetic properties suitable for a controlled release coating made in accordance with the teachings of the present invention. Physical characteristics include durability and elasticity/ductility, chemical characteristics include solubility and/or miscibility and biological characteristics include biocompatibility. The drug release kinetic should be either near zero-order or a combination of first and zero-order kinetics.

Copolymer: As used here in a "copolymer" will be defined as ordinarily used in the art of polymer chemistry. A copolymer is a macromolecule produced by the simultaneous or step-wise polymerization of two or more dissimilar units such as monomers. Copolymer shall include bipolymer (two dissimilar units) terpolymer (three dissimilar units) etc.

Drug(s): As used herein "drug" shall include any bioactive agent having a therapeutic effect in an animal. Exemplary, non limiting examples include anti-proliferatives including, but not limited to, macrolide antibiotics including FKBP 12 binding compounds, estrogens, chaperone inhibitors, protease inhibitors, protein-tyrosine kinase inhibitors, peroxisome proliferator-activated receptor gamma ligands (PPARγ), hypothemycin, nitric oxide, bisphosphonates, epidermal growth factor inhibitors, antibodies, proteasome inhibitors, antibiotics, anti-sense nucleotides and transforming nucleic acids.

Ductility: As used herein "ductility, or ductile" is a polymer attribute characterized by the polymer's resistance to fracture or cracking when folded, stressed or strained at operating temperatures. When used in reference to the polymer coating compostions of the present invention the normal operating temperature for the coating will be between room temperature and body temperature or approximately between 15° C. and 40° C. Polymer durability in a defined environment is often a function of its elasticity/ductility.

Glass Transition Point: As used herein "glass transition point" or "Tg" is the temperature at which an amorphous polymer becomes hard and brittle like glass. At temperatures above its Tg a polymer is elastic or rubbery; at temperatures below its Tg the polymer is hard and brittle like glass. Tg may be used as a predictive value for elasticity/ductility.

Homopolymer: As used herein "homopolymer" shall mean a polymer being composed of a single monomer.

Hydrophillic: As used herein in reference to the bioactive agent, the term "hydrophilic" refers to a bioactive agent that has a solubility in water of more than 200 micrograms per milliliter.

Hydrophobic: As used herein in reference to the bioactive agent the term "hydrophobic" refers to a bioactive agent that has a solubility in water of no more than 200 micrograms per milliliter.

Polymer subunits: As used herein "polymer subunit" or "subunit" refers to the polymer's individual molecular building blocks. In homopolymers the subunits are identical monomers such as polyethylene or polystyrene. However, copolymers can have numerous possible configurations. Bipolymers are the simplest copolymer and will be used in the following example. Bipolymers are composed of two dissimilar subunits. The subunits can be separate monomers, or oligomers. For example, a bipolymer having monomeric subunits is composed of two monomers such as ethylene (E) and styrene (S). The polymer chain can be random (for example, DNA and polypeptides are quintessential random polymers), non-random, blocked or segmented. In random bipolymers, as the name implies, there is no defined order to the monomer sequence, for example—EESESSEESSES— (of course reaction kinetics may favor one coupling reaction over another; these examples are merely for illustrative purposes). Non-random bipolymers would have an alternating configuration such as—ESESESESESESES—. Block copolymers have a high number of covalently bonded repeat subunits such as—EEEEEEEESSSSSSSS-SEEEEEEEEE—(ABA configuration) or—EE-EEEEEEEESSSSSSSSSSS—(an ABn configuration). Finally, segmented bipolymers have a small number of repeat subunits such as—EESSEESSEESS—. If a third polymer is added, a terpolymer results. For example, say acrylic acid is added (A). A random terpolymer would look like—AAESASSEAEESAAESEASEASEA—. A non-random terpolymer would look like—ASEASEASEASEASE-ASEASE—. And a block terpolymer may look like this—AAASSSEEEAAASSSEEEAAASSSEEE—. There are myriad other possible configurations depending on the number of monomeric subunits involved. Still more complex copolymers are possible when the subunits are polymers themselves (oligomeric subunits). Copolymer and terpolymers composed of oligomeric subunits often resemble random and block polymers in their behavior and therefore will not be considered further. Finally, this brief description of polymer primary structure (the chain makeup) did not consider graft polymers (where monomer and polymer side chains are attached as pendent groups to the primary polymer chain) or crosslinking between chains and/or pendent groups (secondary polymer structure). However, any and all of the primary and secondary structures discussed herein and variations thereon are considered within the scope of the present invention.

Units of Measure: As used herein solubility parameters for polymers and solvents will be expressed in $\delta$ as originally defined by Hildebrand and Hansen (see for example Properties of Polymers. 1990. $3^{rd}$ edition. D. W. van Krevelen. Elsevier press. ISBN 0-444-88160-3. The entire contents or which are herein incorporated by reference). $\delta$ is a thermodynamic unit expressed in $J^{1/2}/cm^{3/2}$. However, the reader is cautioned that beginning in 1984 a new value for $\delta$ has been adopted and designated $\delta(SI)$ and expressed in $MPa^{1/2}$. To convert between $\delta$ ($J^{1/2}/cm^{3/2}$) and $\delta(SI)$ ($MPa^{1/2}$) multiply $\delta$ by 2.0045 or divide $\delta(SI)$ by 0.488.

DETAILED DESCRIPTION OF THE INVENTION

The present invention is directed at engineering polymers that provide optimized drug-eluting medical devices coatings. Specifically, polymers made in accordance with teachings of the present invention provide durable biocompatible coatings for medical devices intended for use in hemodynamic environments. In one embodiment of the present invention vascular stents are coated using the polymer compositions of the present invention. Vascular stents are chosen for exemplary purposes only. Those skilled in the art of material science and medical devices will realize that the polymer compositions of the present invention are useful in coating a large range of medical devices. Therefore, the use of the vascular stent as an exemplary embodiment is not intended as a limitation.

Vascular stents present a particularly unique challenge for the medical device coating scientist. Vascular stents (hereinafter referred to as "stents") must be flexible, expandable, biocompatible and physically stable. Stents are used to relieve the symptoms associated with coronary artery disease caused by occlusion in one or more coronary artery. Occluded coronary arteries result in diminished blood flow to heart muscles causing ischemia induced angina and in severe cases myocardial infarcts and death. Stents are generally deployed using catheters having the stent attached to an inflatable balloon at the catheter's distal end. The catheter is inserted into an artery and guided to the deployment site. In many cases the catheter is inserted into the femoral artery or of the leg or carotid artery and the stent is deployed deep within the coronary vasculature at an occlusion site.

Vulnerable plaque stabilization is another application for coated drug-eluting vascular stents. Vulnerable plaque is composed of a thin fibrous cap covering a liquid-like core composed of an atheromatous gruel. The exact composition of mature atherosclerotic plaques varies considerably and the factors that effect an atherosclerotic plaque's make-up are poorly understood. However, the fibrous cap associated with many atherosclerotic plaques is formed from a connective tissue matrix of smooth muscle cells, types I and III collagen and a single layer of endothelial cells. The atheromatous gruel is composed of blood-borne lipoproteins trapped in the sub-endothelial extracellular space and the breakdown of tissue macrophages filled with low density lipids (LDL) scavenged from the circulating blood. (G. Pasterkamp and E. Falk. 2000. Atherosclerotic Plaque Rupture: An Overview. J. Clin. Basic Cardiol. 3:81-86). The ratio of fibrous cap material to atheromatous gruel determines plaque stability and type. When atherosclerotic plaque is prone to rupture due to instability it is referred to a "vulnerable" plaque. Upon rupture the atheromatous gruel is released into the blood stream and induces a massive thrombogenic response leading to sudden coronary death. Recently, it has been postulated that vulnerable plaque can be stabilized by stenting the plaque. Moreover, vascular stents having a drug-releasing coating composed of matrix metalloproteinase inhibitor dispersed in, or coated with (or both) a polymer may further stabilize the plaque and eventually lead to complete healing.

As used herein after "treatment site" shall mean a vascular occlusion, a vulnerable plaque region or an aneurysm.

Once positioned at the treatment site the stent or graft is deployed. Generally, stents are deployed using balloon catheters. The balloon expands the stent gently compressing it against the arterial lumen clearing the vascular occlusion or stabilizing the plaque. The catheter is then removed and the stent remains in place permanently. Most patients return to a normal life following a suitable recovery period and have no reoccurrence of coronary artery disease associated with the stented occlusion. However, in some cases the arterial wall's initma is damaged either by the disease process itself or as the result of stent deployment. This injury initiates a complex biological response culminating is vascular smooth muscle cell hyperproliferation and occlusion, or restenosis at the stent site.

Recently significant efforts have been devoted to preventing restenosis. Several techniques including brachytherapy, excimer laser, and pharmacological techniques have been developed. The least invasive and most promising treatment modality is the pharmacological approach. A preferred pharmacological approach involves the site specific delivery of cytostatic or cytotoxic drugs directly to the stent deployment area. Site specific delivery is preferred over systemic delivery for several reasons. First, many cytostatic and cytotoxic drugs are highly toxic and cannot be administered systemically at concentrations needed to prevent restenosis. Moreover, the systemic administration of drugs can have unintended side effects at body locations remote from the treatment site. Additionally, many drugs are either not sufficiently soluble, or too quickly cleared from the blood stream to effectively prevent restenosis. Therefore, administration of anti-restenotic compounds directly to the treatment area is preferred.

Several techniques and corresponding devices have been developed to deploy anti-restenotic compounds including weeping balloon and injection catheters. Weeping balloon catheters are used to slowly apply an anti-restenotic composition under pressure through fine pores in an inflatable segment at or near the catheter's distal end. The inflatable segment can be the same used to deploy the stent or separate segment. Injection catheters administer the anti-restenotic composition by either emitting a pressurized fluid jet, or by directly piercing the artery wall with one or more needle-like appendage. Recently, needle catheters have been developed to inject drugs into an artery's adventitia. However, administration of anti-restenotic compositions using weeping and injection catheters to prevent restenosis remains experimental and largely unsuccessful. Direct anti-restenotic composition administration has several disadvantages. When anti-restenotic compositions are administered directly to the arterial lumen using a weeping catheter, the blood flow quickly flushes the anti-restenotic composition down stream and away from the treatment site. Anti-restenotic compositions injected into the lumen wall or adventitia may rapidly diffuse into the surrounding tissue. Consequently, the anti-restenotic composition may not be present at the treatment site in sufficient concentrations to prevent restenosis. As a result of these and other disadvantages associated with catheter-based local drug delivery, investigators continue to seek improved methods for the localized delivery of anti-restenotic compositions.

Figure 2:
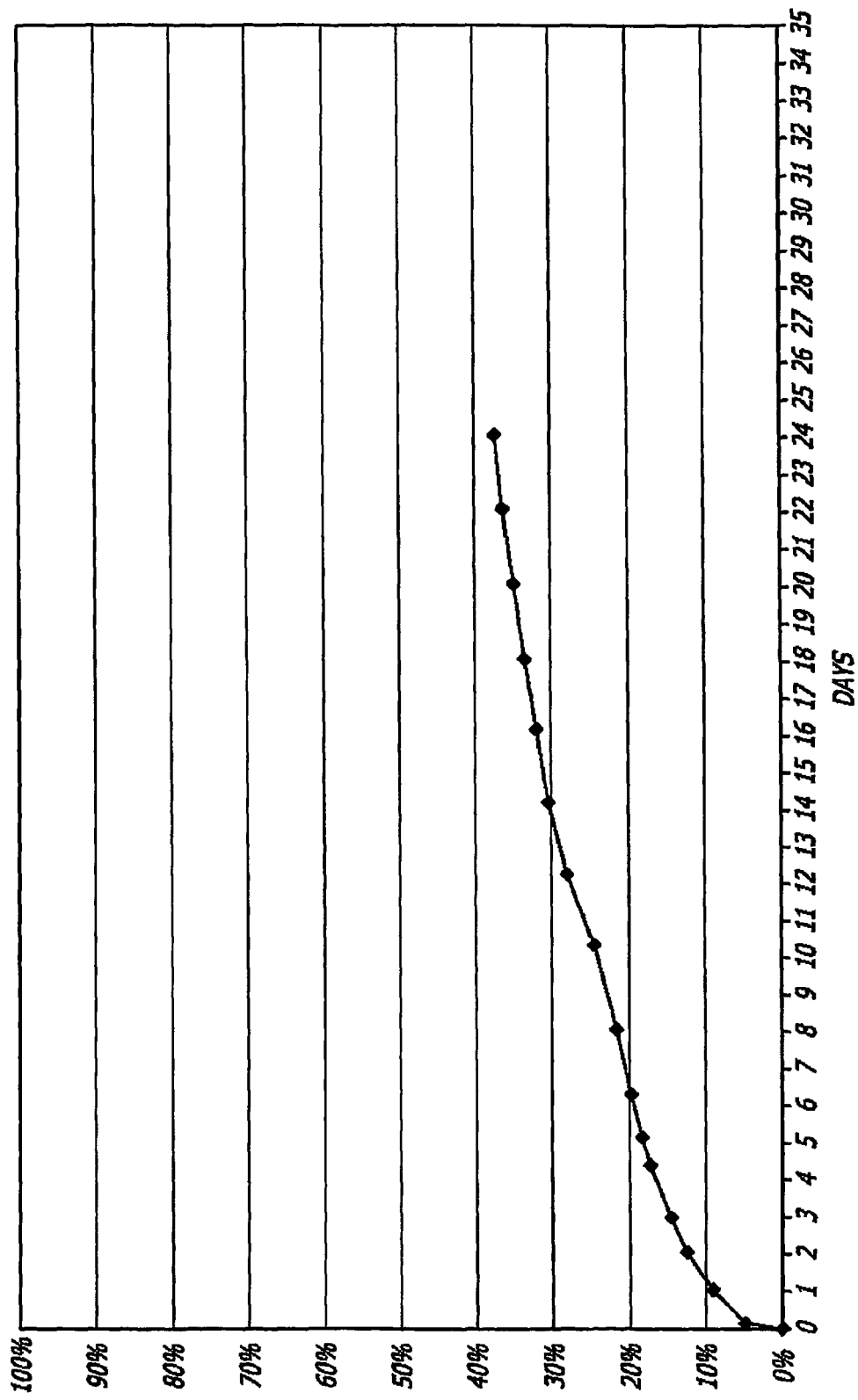
FIG. 2 graphically depicts idealized zero-order kinetics associated with drug release from a polymer coating.

The most successful method for localized anti-restenotic composition delivery developed to date is the drug-eluting stent. Many drug-eluting stent embodiments have been developed and tested. However, significant advances are still necessary in order to provide safe and highly effective drug delivery stents. One of the major challenges associated with stent-based anti-restenotic composition delivery is controlling the drug delivery rate. Generally speaking drug delivery rates have two primary kinetic profiles. Drugs that reach the blood stream or tissue immediately after administration follow first-order kinetics. FIG. 1 graphically depicts idealized first-order kinetics. First-order drug release kinetics provide an immediate surge in blood or local tissue drug levels (peak levels) followed by a gradual decline (trough levels). In most cases therapeutic levels are only maintained for a few hours. Drugs released slowly over a sustained time where blood or tissue concentrations remains steady follow zero-order kinetics. FIG. 2 graphically depicts idealized zero-order kinetics. Depending on the method of drug delivery and tissue/blood clearance rates, zero-order kinetics result in sustained therapeutic levels for prolonged periods. Drug-release profiles can be modified to meet specific applications. Generally, most controlled release compositions are designed to provide near zero-order kinetics. However, there may be applications where an initial burst, or loading dose, of drug is desired (first-order kinetics) followed by a more gradual sustained drug release (near zero-order kinetics). The present invention provides methods for designing polymeric compositions having drug-release profiles that follow first-order kinetics, zero-order kinetics and first and zero-order kinetic combinations. Thus, among other qualities, the present invention provides polymeric controlled release coatings optimized for any application, specifically coatings for vascular implants.

Controlling the drug-release rate from medical device surfaces is challenging. This challenge is even greater when the device is a vascular stent. Stents are deployed in a physiological and anatomical environment that exposes the device and its coatings to the physical forces associated with blood circulation. Blood circulates throughout the body in a closed system of arteries and veins collectively referred to as blood vessels. The physical forces associated with blood circulation are referred to as hemodynamic forces and include the mechanical and hydrodynamic forces. For example, blood flow in and around vessel obstructions, including medical implants can result in turbulent blood flow. Turbulent blood flow can cause shear forces which have an eroding effect on exposed surfaces. Furthermore, there are mechanical forces associated with blood circulation such as the expansion and contraction of blood vessels and adjacent muscles and organs. These mechanical forces may cause vascular implants to bend, twist and strain and may also induce friction at the interface between the blood vessel lumen wall and vascular implant's surface. Finally, significant strain is placed on the stent body and coating during deployment. Stents are generally compressed on the distal end of the catheter and then expanded at the deployment site. The combination of pre-deployment compression and deployment expansion causes significant mechanical stress to the stent and any associated coating.

The present invention is directed at optimized drug releasing medical device coatings suitable for use in hemodynamic environments. The coatings of the present invention are composed of polymers having at least one bioactive agent dispersed therein. The polymeric compositions of the present invention have been specifically formulated to provide medical device coatings that tenaciously adhere to medical device surfaces (do not delaminate), flex without fracturing (ductile), resist erosion (durable), are biocompatible and release a wide variety of drugs at controlled rates.

Polymers have been used as medical device coatings for decades to enhanced biocompatibility and erosion resistance. Moreover, in certain applications polymer coatings may also provide electrical insulation. It is also well known in the art that polymers can act as reservoirs and/or diffusion barriers to control biological agent elution rates. Numerous examples were discussed in the preceding "Background of the Invention" section.

Recently, coatings have been applied to implantable medical devices such vascular stents, vascular stent grafts, urethral stents, bile duct stents, catheters, inflation catheters, injection catheters, guide wires, pace maker leads, ventricular assist devices, and prosthetic heart valves. Devices such as these are generally subjected to flexion strain and stress during implantation, application or both. Providing flexible medical devices such as stents with stable biocompatible polymer coatings is especially difficult.

There are two basic molecular morphologies that define a polymer's tertiary solid-state structure. Polymers may be either semi-crystalline or amorphous depending on the nature of the polymer subunit. Semi-crystalline polymers are ridged and brittle at any temperature below their melting point and are generally not suitable for coating flexible medical devices such as stents. In addition, drugs or bioactive agents cannot stay in the polymer crystal region, therefore, the drugs or bioactive agents loading is limited. Amorphous polymers, on other hand, can be either rigid or elastic/ductile depending on its glass transition point. The glass transition point of an amorphous polymer is the temperature above which the amorphous polymer is elastic/ductile and flexible. For stent application it is desirable that the Tg be below body temperature. Many polymeric compostions have glass transition points substantially above body temperature and are thus in the glassy or rigid state when the device is deployed and remains so once the device is implanted. Polymers in the "glassy" state are non-elastic/ductile and prone to cracking, fracturing and delaminating when the stent is flexed. Polymer coatings susceptible to fracture and delaminating are especially undesirable when used on stents. Small polymer particles that separate from a delaminated or fractured stent coating may be carried by the blood flow downstream where they can lodge in capillaries and obstruct blood flow to critical regions of the heart. Therefore stents and other flexible medical devices should have polymer coatings that are elastic/ductile and adhere to the device surface well. Generally, this requires that coating polymers be amorphous and have glass transition points below body temperature.

However, polymers having extremely low Tgs are undesirable when used to coat devices that are subjected to continual hemodynamic forces. As general rule, the lower the Tg the more rubbery a polymer becomes. More rubbery polymers can be tacky and less durable and are more likely to break down when exposed to hemodynamic induced stress and wear than less rubbery ones. This is partially due to the fact that the more rubbery polymers have higher coefficients of friction and possess less structural integrity. Therefore, polymers having extremely low Tgs should not be the dominant polymer in polymer blends or copolymer compostions when designing coating polymers intend for stents and other vascular implants. In addition, extremely low Tg (e.g., rubbery) polymers tend to release drugs or bioactive materials at undesirably fast rates due to their high free volumes.

In addition to the aforementioned structural and drug releasing profile considerations, polymers used as stent coatings must also be biocompatible. Biocompatibility encompasses numerous factors that have been briefly defined in the preceding "Definition of Terms" section. The need for a polymer to be biocompatible significantly limits the number of available options for the material scientist. Moreover, these options are further limited when the polymer coating is used on a device that is continuously exposed to hemodynamic forces. For example, stent coatings must remain non-thrombogenic, non-inflammatory and structurally stable for prolong time periods.

There are generally two large, and to some extent overlapping, categories of biocompatible polymers suitable as medical device coatings: bioerodable (including bioresorbable polymers) and non-bioerodable polymers. Coating compositions of the present invention are principally directed at the latter. However, the present invention's methods are equally applicable to bioerodable and non-bioerodable polymer coatings. The remaining discussion and exemplary embodiments will be directed at non-bioerodable polymers.

Non-erodable polymers can be hydrophilic, hydrophobic or amphiphilic depending on the polarity of the monomers used and the ratio of hydrophobic to hydrophilic monomers. Hydrophilic polymers are polar molecules that are miscible with polar solvents and are generally lubricious while contacting body fluids. Hydrophilic polymers are often used in biomedical applications to produce lubricious hydrogels. Hydrogels, include polymer compositions that can absorb more than 20% its weight in water while maintaining a distinct three-dimensional structure. This definition includes dry polymers that swell in aqueous environments in addition to the water-swollen polymer compositions. Hydrogels are divided into two general classes and "aerogels" and "xerogels." Aerogels are porous hydrogels that absorb water into its macropous structure without exhibiting significant swelling. Moreover, aerogels do not collapse and contract upon drying. Consequently, aerogels are ideally suited for applications that require high water absorbency with minimum change is polymer volume is desired. In contrast xerogels are nonporous gels absorb water into the polar regions of the polymer's macro structure resulting in considerable swelling and corresponding volume increase.

Hydrogels are an exceptionally diverse group of materials. Virtually all hydrophilic polymers can be crosslinked to produce hydrogels, whether the polymer is of biological origin, semi-synthetic, or wholly synthetic. Hydrogels properties such as equilibrium swelling degree, sorption kinetics, solute permeability, and their in vivo performance characteristics possess properties that make them suitable for drug delivery applications. The equilibrium swelling degree or sorption capacity (swollen volume/dry volume) is the single most important property of a hydrogel and directly influences the other properties. Unfortunately, the mechanical strength of a gel declines in rough proportion to the swelling degree, although strength is usually of lesser concern for drug delivery than the other four properties. However, when mechanical strength is important for a hydrogel, it can be bonded onto a support made of plastic, ceramic or metal. The composite system then gains the mechanical strength of the substrate along with the useful drug delivery properties of the hydrogel.

These properties, either singly or in combination, have led to widespread interest in the use of hydrogels for drug delivery. These materials can be used to protect labile drugs from denaturants, control the release rate of the therapeutic agent, or help target release to a chosen site within the body. They can be made as oral dosage forms, suppositories, injectable micro/nanoparticles, or implants at any site within the body, even when blood contact is required. (For examples see: S. H. Gehrke "Synthesis and Properties of Hydrogels for Used for Drug Delivery," Transport in Pharmaceutical Sciences, G. Amidon and P. I. Lee, Eds., Marcel Dekker, New York, in press (1999). The entire contents of which are herein incorporated by reference). However, hydrogel polymers can be unstable in a hemodynamic environment and lack physical integrity because their high water content. Moreover, many hydrophobic drugs do not disperse well in hydrogels and therefore hydrogels are not suitable drug delivery platforms for some hydrophobic bioactive agents.

However, the swellability of hydrogels and other hydrophilic polymers can be a relevant consideration when making the compatibilized drug-releasing coatings of the present invention. Swellabilities of polymers in water can be easily determined. It should be understood, however, that the swellability results from incorporation of water and not from an elevation in temperature. As water is incorporated into a swelling polymer the free volume increases. As a result, the rate at which a drug will diffuse from a polymer matrix increases and the polymer becomes increasingly elastic/ductile. Therefore, by selecting relatively low and high swell polymers that are miscible, the dissolution rate and can be adjusted (the effect of increasing free volume on elasticity/ductility will be discussed in more detail below). This is particularly true for polymer matrices incorporating high molecular weight bioactive agents and can be a major contributing factor to elution rates for matrix systems as will be discussed more fully below.

Preferably, a polymer having a relatively high swellability is combined with a polymer having a relatively low swellability. For example, a miscible polymer blend for an active agent having a molecular weight of greater than 1200 g/mol includes polyvinyl pyrollidone-vinyl acetate copolymer, which has a swellability of greater than 100%, and poly(ether urethane), which has a swellability of 60%. By combining such high and low swell polymers, the active agent delivery system can be tuned for the desired dissolution time of the active agent.

Swellabilities of the miscible polymer blends are also used as a factor in determining the combinations of polymers for a particular active agent. For delivery systems in which the active agent has a molecular weight of greater than 1200 g/mol, whether it is hydrophilic or hydrophobic, polymers are selected such that the swellability of the blend is greater than 10% by volume. The swellability of the blend is evaluated without the active agent incorporated therein.

Hydrophobic polymers such as polytetrafluoroethylene (PTFE AKA Teflon®) do not swell but can also be biocompatible. Teflon® has an extremely low coefficient of friction and is one of the most widely used hydrophobic biocompatible polymers. However, PTFE's slipperiness makes it difficult to handle and manipulate. Moreover, PTFE is a stiff chemically inert polymer and bonds poorly to surfaces. Furthermore, PTFE's extremely hydrophobic nature significantly limits its chemical compatibility with many bioactive agents. Recently, nanoporous PTFE has been developed that can be used as a barrier coating, or cap coat, that mediates bioactive agent release from an underlying drug reservoir (Advanced Surface Engineering, Inc. Eldersburg, Md.). However, nanoporous PTFE coatings are expensive and the application process is not compatible with all medical device surfaces and drug categories. Consequently, the usefulness of PTFE as a medical device coating is limited. There are many other biocompatible hydrophobic polymers; however, many of these have a high coefficient of frictions which is undesirable in a hemodynamic environment. Moreover, many hydrophilic drugs do not disperse well in hydrophobic polymer and therefore are not suitable drug delivery platforms for many hydrophilic bioactive agents.

Therefore, there are four specific attributes that the stent coating polymers made in accordance with the teachings of the present invention should possess. The polymer compositions of the present invention should be biocompatible, durable, elastic/ductile and possess a predetermined drug release profile. Prior to the present invention polymer coating design was largely a matter of trial and error. Previously, material scientists based their polymer coating compositions on best guesses and previous experience. Slight modifications were made randomly and the resulting polymer compositions were tested in vitro and in vivo. Unsuccessful polymers were eliminated from further consideration and the successful polymer ultimately selected from myriad potential candidates. The present invention provides methods for reproducibly balancing the four critical parameters of biocompatibility, durability, elasticity/ductility and drug release profile when designing controlled release polymer coatings. Moreover, the present invention provides novel polymer compositions made in accordance with the teachings of the present invention.

One of the most fundamental physical chemical properties that must be considered when selecting polymers for use as controlled release coatings is the polymer's solubility parameters. The present inventors have developed a novel method of using solubility parameters for designing polymeric compositions useful as controlled release coatings for devices deployed in hemodynamic environments. At its most basic level, the present invention employs principles of polymer physical chemistry to match polymeric compositions with drugs so that the resulting controlled release coatings have both optimum physical attributes and drug release kinetic profiles.

As used hereinafter the compositions of the present invention will be referred to as "controlled release coatings." This term shall refer to a polymeric composition that has optimum physical characteristics such including biocompatibility, durability, elasticity/ductility in addition to a predetermined optimum drug releasing kinetic profile.

Polymer solubility parameters as a function of a polymer's cohesive properties were known to be a direct expression of the polymer's behavior in aqueous and organic solvents as early as 1916. However, it was not until 1949 that Hildebrand proposed the term solubility parameter and assigned the symbol "$\delta$" to represent a polymer's behavior in specific solvents; as previously discussed, "$\delta$" will be expressed in $J^{1/2}/cm^{3/2}$. However, Hildebrand had only considered dispersive forces between various structural units when determining solvent/polymer solubility parameters. Later, Hansen et al. established that the interaction between polar groups and hydrogen bonding contributed significantly to the total cohesive energy, and thus the solubility behavior of many liquids and amorphous polymers. Therefore, Hansen defined a polymer's total solubility ($\delta_T$) as the interaction between three distinct values: dispersion force ($\delta_D$), polar force ($\delta_P$), and hydrogen bonding force ($\delta_H$) (see van Krevelen at pages 189-226). As used herein $\delta_T$ will be used to refer to the final solubility parameter of a controlled release coating made in accordance with the teachings of the present invention. As will be evident from the teachings that follow, a controlled release coating may be a terpolymer, or a blend of copolymers and/or copolymers and homopolymers.

The present inventors have used the Hansen solubility parameters to optimize controlled release coating compositions for stents. The present inventors have determined that the optimum drug release kinetic profile occurs when the polymer's solubility parameter closely matches the drug's. However, merely matching candidate drug's solubility with polymer's $\delta_T$ does not always result in a functional controlled release coating. As discussed extensively above there are three additional criteria that a successful controlled release coating must meet. The present inventors have determined that various homoploymers, copolymer and combinations thereof, can be designed by balancing the Hansen solubility parameters of the polymer subunits and/or individual polymers in a blend.

Generally speaking for an individual homopolymer's $\delta$ equals $[\delta_D^2+\delta_P^2+\delta_H^2]^{1/2}$. In a copolymer the combined $\delta$s, or total $\delta$ ($\delta_T$), equals $\Sigma X\delta_1+X\delta_2+X\delta_3+X\delta_4\ldots$ where X equals the percentage of each polymer subunit (T1, T2, T3 etc) in the total polymer. Likewise, for a polymer blend the combined $\delta_T$ equals $\Sigma X\delta_{T1}+X\delta_{T2}+X\delta_{T3}+X\delta_{T4}\ldots$ where X equals the percentage of each individual polymer in the blend (T1, T2, T3 etc). Therefore, the present inventors determined that the $\delta_T$ can be adjusted to match the $\delta$ for any given drug.

However, the present inventors have also determined that a copolymer's biocompatibility, elasticity/ductility and durability can be optimized by altering the ratio of polymeric subunits that favor one property over another. For example, ductility and durability are roughly a function of the polymer's Tg. The lower the Tg, the more ductile the polymer becomes. However, below a certain point the polymer becomes too rubbery and its durability is adversely effected. Moreover, extremely rubbery polymers possess greater first-order kinetics than near zero-order kinetics, consequently, extremely low Tgs are to be avoided.

The present inventors have developed a system for controlled release coating design that is conceptually similar to how the individual Hansen solubility parameters affect a polymer's $\delta$. For example, hydrogen bonding capacity contributes more significantly to a controlled release coating's biocompatibility than other factors. Therefore, polymers having high hydrogen bonding potential such as poly(N-vinyl pyrrolidone) increase biocompatibility.

Elasticity/ductility increases as the polymer's Tg decreases. Tg in turn decreases as the polymer's free volume increases. Free volume corresponds to the unoccupied regions accessible to segmental motions. Free volume in turn is affected by several factors including swellability, the number and size of pendent groups present on polymer subunits and the extent and degree of cross linking. The affects of free volume on Tg are best appreciated with reference to examples. Compare the effects on Tg caused by adding two different alkyl ester monomers to a terpolymer. For this example assume that the terpolymer is composed of 30% vinyl acetate, 40% Y-methacrylate and 30% N-vinyl pyrrolidone. If Y equals hexyl, the resulting terpolymer has a calculated Tg of 21° C. and a calculated $\delta$ of approximately 21. However, if lauryl methacrylate is substituted for hexyl-methacrylate the polymers' Tg to −11 but $\delta$ remains approximately 21.

The preceding example demonstrates the effect that pendent chain group size has on Tg. Note that the larger pendent group on the lauryl methacrylate monomer dramatically decreases Tg as compared to hexyl-methacrylate while having no effect on $\delta$. However, as previously stated, even though $\delta$ remains the same, the release kinetics of the terpolymer using lauryl methacrylate in place of hexyl-methacrylate are not optimum. The lauryl methacrylate-containing polymer exhibited near first-order kinetics when tested. Therefore, the present inventors have discovered that the pendent group size on hydrophobic polymers such as alkyl esters can affect polymer dispersive forces ($\delta_D$) and which in turn can affect release kinetics and Tg. However, Tg can also be affected by monomer polarity ($\delta_P$). In one embodiment of the present invention vinyl acetate is used to modulate polymer polarity. Vinyl acetates have polar groups that increase the intermolecular forces and decrease free volume. As free volume decreases, Tg increases.

In another embodiment compatible polymer blends are made using the teachings of the present invention. As used herein compatible polymer blends shall mean two or more chemically distinct polymers, including homopolymers and copolymers that form a stable mixture that does not separate on standing or during prolonged use and possess the other desired physical and chemicals properties discussed herein. Methods for compatibilizing two or more polymers with at least one bioactive agent are provided accordingly. A first polymer composition known to have certain desirable properties such as biocompatibility and elasticity/ductility is selected. However, the Tg of the first polymer may be below the desired range and thus have poor controlled release properties (for example it may have a first-order kinetic profile). Moreover, the first polymer may not have a $\delta$ compatible with the bioactive agent. Consequently, a second polymer composition having solubility parameters and Tg that balance the first polymer's Tg and $\delta$ can be blended with the first polymer composition to create an optimum controlled release coating.

For example, and not intended as a limitation, polyethylene-co-vinyl acetate (PEVAC) copolymers are durable, elastic/ductile and exhibit good adhesion to metals. However, PEVAc's low Tg renders the polymer tacky and prone to first-order drug release kinetics. Therefore, it may be desirable to create polymer blends using PEVAc as the first polymer composition and a second polymer that is compatible with PEVAc. Moreover, the second polymer component should have a Tg that compensates for PEVAc's low Tg and also possess $\delta$ values that provide a $\delta_T$ for the polymer blend that approximately matches the bioactive agent's $\delta$. However, in order to assure that the polymer blend that has a $\delta_T$ and Tg optimized for a controlled release coating the first and second polymer composition must be miscible. In this example, because PEAVc contains vinyl acetate the second polymer composition should possess vinyl acetate monomers to increase miscibility. This approach helps compatibilize the second polymer composition with PEVAc and helps provide a compatible polymer blend having an optimized drug release kinetic profile.

Therefore, optimized controlled release coatings require that both $\delta$ values and Tg be considered when selecting polymer subunits. The design of a controlled release coating made in accordance with the teachings of the present invention begins with selecting the drug or drug-combination to be delivered and the desired drug release kinetic profile. Next the drug's solubility parameter is determined and the general chemical make up of the molecule is considered, that is, is the drug polar or non-polar? Then, starting with the basic assumption that like-dissolves-like, polymer units having a $\delta_P$ approximately equal to the drug are selected. However, it is important to avoid selecting alkyl esters having extremely large pendent groups that may drop the controlled release coating's Tg below that optimum for the desired release kinetics. Polymer subunits are then selected having $\delta_D$'s that will balance the adverse effects on Tg caused by polymers having an unfavorable $\delta_P$. Finally, polymer subunits having $\delta_H$'s necessary for good biocompatibility are added to the list of candidate polymeric subunits.

Adjustments to the theoretical polymer blends can be made by varying polymer subunit concentrations in accordance with the teachings of the present invention until a $\delta_T$ approximately equal to the drug's $\delta$ is achieved. If the Tg drops below an acceptable range for the drug release kinetics desired the $\delta_P$ and $\delta_D$ components can be adjusted, or slightly different polymeric subunits can be selected as necessary. Finally, once the desired Tg range is reached the final concentration of $\delta_H$ subunits can be adjusted to assure optimum biocompatibility. The final polymer, or polymer blend, will have a $\delta_T$ approximately equal to the drug's $\delta$ and a Tg below body temperature, but not so low as to adversely affect the drug release kinetic profile desired. In one embodiment of the present invention $\delta$ is between approximately 15 $J^{1/2}/cm^{3/2}$ to 21 $J^{1/2}/cm^{3/2}$ and Tg is between approximately 10° C. and 35° C.

Persons having ordinary skill in the art will realize that the above discussion is intended as a guide and that minor variations can be made to the order of polymer selection and target Tg and $\delta$ values without deviating from the sprit of the invention. Moreover it is with the scope of the present invention to add polymer modifiers including crosslinking reagents and polymer grafts to control swelling and enhance over all durability and drug release kinetics.

However, release rate is not entirely a function of drug-polymer compatibility. Coating configurations, polymer swellability and coating thickness also play roles. When the medical device of the present invention is used in the vasculature, the coating dimensions are generally measured in micrometers (μm). Coatings consistent with the teaching of the present invention may be a thin as 1 μm or a thick as 1000 μm. There are at least two distinct coating configurations within the scope of the present invention. In one embodiment of the present invention the drug-containing coating is applied directly to the device surface or onto a polymer primer coat such a parylene or a parylene derivative. Depending on the solubility rate and profile desired, the drug is either entirely soluble within the polymer matrix, or evenly dispersed throughout. The drug concentration present in the polymer matrix ranges from 0.1% by weight to 80% by weight. In either event, it is most desirable to have as homogenous of a coating composition as possible. This particular configuration is commonly referred to as a drug-polymer matrix.

In another embodiment of the present invention a drug-free polymer barrier, or cap, coat is applied over the drug-containing coating. The drug-containing coating serves as a drug reservoir. Generally, the concentration of drug present in the reservoir ranges from abort 0.1% by weight to as much as 100%. The barrier coating participates in the controlling drug release rates in at least three ways. In one embodiment the barrier coat has a solubility constant different from the underlying drug-containing coating. In this embodiment the drugs diffusivity through the barrier coat is regulated as a function of the barrier coating's solubility factors. The more miscible the drug is in the barrier coat, the quicker it will elute form the device surface and visa versa. This coating configuration is commonly referred to as a reservoir coating.

In another embodiment the barrier coat comprises a porous network where the coating acts as a molecular sieve. The larger the pores relative to the size of the drug, the faster the drug will elute. Moreover, intramolecular interactions will also determine the elution rates. The intramolecular interactions having the greatest net effect on drug elution include the relative hydrophobicity/hydrophilicity ($\delta_H$) of the drug-polymer interaction. These factors have already been discussed above and apply to both the drug-containing coating as well as the barrier coating, the less intramolecular interaction between the drug and polymer barrier coat, the faster the drug will transit the porous network and enter the neighboring tissues. Persons having ordinary skill in the art of material science in combination with the teachings herein will readily understand that many variations on the cap coat and drug-eluting coatings can be made to tune the target diffusivity of the present invention.

Swellability is also an important factor. Polymer free volume increases proportionally to increases in swellability. Therefore, drug elution rate increases with increasing swellability. As a result, for the purposes of the present invention the total swellability of the polymer blend used with bioactive agents having molecular weights less or than about 1200 g/mol and polymer blends having a $\delta_T$ greater than 25 $J^{1/2}/cm^{3/2}$ should not exceed 10% by volume. Moreover, the total swellability should not exceed 10% by volume when the active agents have molecular weights greater than about 1200 g/mol and the polymer blend has a $\delta_T$ less than 25 $J^{1/2}/cm^{3/2}$. In both cases this remains true regardless of whether the bioactive agent is hydrophilic or hydrophobic.

Finally, returning to coating thickness, while thickness is generally a minor factor in determining overall drug-release rates and profile, it is never-the-less an additional factor that can be used to tune the coatings. Basically, if all other physical and chemical factors remain unchanged, the rate at which a given drug diffuses through a given coating is directly proportional to the coating thickness. That is, increasing the coating thickness increases the elution rate and visa versa.

We now turn to another factor that contributes to the compatibilized controlled release coatings of the present invention. As mentioned earlier, coating intended for medical devices deployed in a hemodynamic environment must possess excellent adhesive properties. That is, the coating must be stably linked to the medical device surface. Many different materials can be used to fabricate the implantable medical devices including stainless steel, nitinol, aluminum, chromium, titanium, ceramics, and a wide range of plastics and natural materials including collagen, fibrin and plant fibers. All of these materials, and others, may be used with the controlled release coatings made in accordance with the teachings of the present invention.

Figure 5:
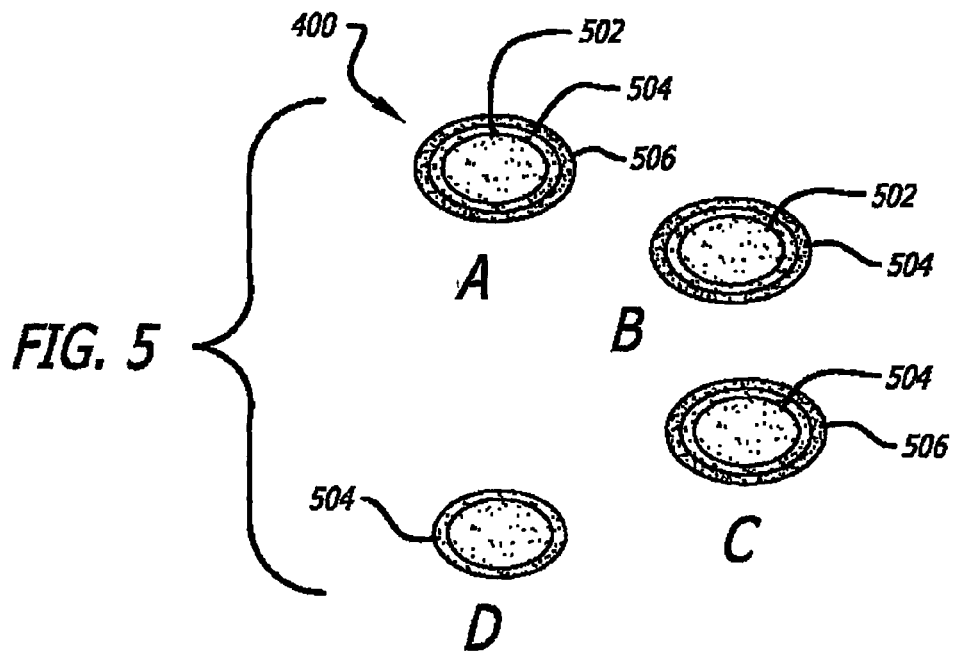
FIG. 5 a-d depict cross sections of the various coating configurations used to provide vascular stents with the controlled release coatings made in accordance with the teachings of the present invention.
Figure 6:
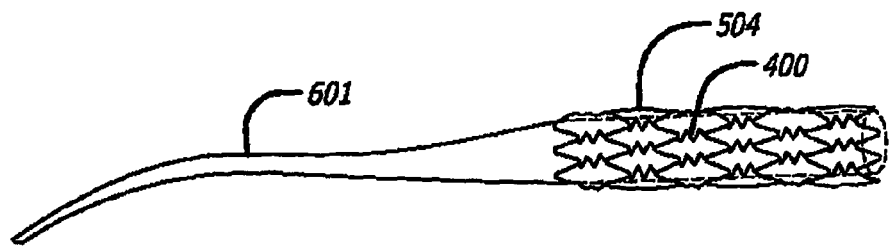
FIG. 6 depicts a vascular stent having a coating made in accordance with the teachings of the present invention mounted on a suitable delivery device—a balloon catheter.
Figure 4:
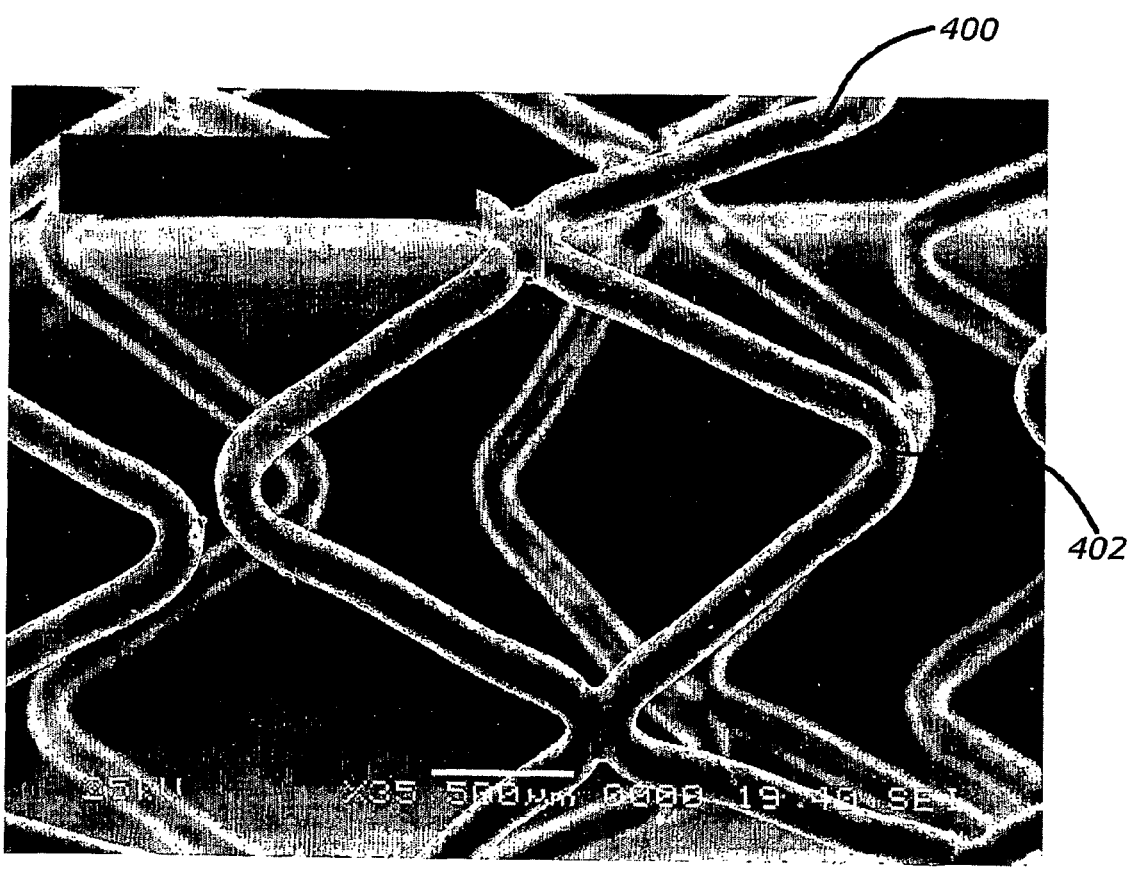
FIG. 4 depicts a medical device, specifically a vascular stent having the coating made in accordance with the teachings of the present invention thereon.

One embodiment of the present invention is depicted in FIG. 4. In FIG. 4 a vascular stent 400 having the structure 402 is made from a material selected from the non-limiting group materials including stainless steel, nitinol, aluminum, chromium, titanium, ceramics, and a wide range of plastics and natural materials including collagen, fibrin and plant fibers. The structure 402 is provided with a coating composition made in accordance with the teachings of the present invention. FIG. 5a-d are cross-sections of stent 400 showing various coating configurations. In FIG. 5a stent 400 has a first polymer coating 502 comprising a medical grade primer, such as but not limited to parylene or a parylene derivative; a second controlled release coating 504; and a third barrier, or cap, coat 506. In FIG. 5b stent 400 has a first polymer coating 502 comprising a medical grade primer, such as but not limited to parylene or a parylene derivative, and a second controlled release coating 504. In FIG. 5c stent 400 has a first controlled release coating 504 and a second barrier, or cap, coat 506. In FIG. 5 d stent 400 has only a controlled release coating 504. FIG. 6 depicts a vascular stent 400 having a coating 504 made in accordance with the teachings of the present invention mounted on a balloon catheter 601.

There are many theories that attempt to explain, or contribute to our understanding of how polymers adhere to surfaces. The most important forces include electrostatic and hydrogen bonding. However, other factors including wettability, absorption and resiliency also determine how well a polymer will adhere to different surfaces. Therefore, polymer base coats, or primers are often used in order to create a more uniform coating surface. In one embodiment of the present invention medical devices, specifically stents, are provided with polymer primer coats that provide inert adhesion layers for the controlled release coatings of the present invention. For example, and not intended as a limitation, parylene C is applied to the stent surface using vapor deposition techniques. Parylene is a hydrophobic, biocompatible, lubricious polymer that is transparent, flexible and meets USP class VI plastic requirements. Moreover, parylene is a gas-phase polymerized composition that completely forms to device surface topologies leaving a thin, pinhole-free base coat that is readily coated with other polymers. Parylene's hydrophobic nature can present challenges to coating scientists. However, when used in accordance with the teaching of the present invention, controlled release polymer compositions can be optimized to assure good long-term adhesion to the primer coat.

The controlled release coatings of the present invention can be applied to medical device surfaces, either primed or bare, in any manner known to those skilled in the art. Applications methods compatible with the present invention include, but are not limited to, spraying, dipping, brushing, vacuum-deposition, and others. Moreover, the controlled release coatings of the present invention may be used with a cap coat. A cap coat as used here refers to the outermost coating layer applied over another coating. For examples, and not intended as a limitation: a metal stent has a parylene primer coat applied to its bare metal surface. Over the primer coat a drug-releasing terpolymer coating or blend of homopolymer, copolymer and terpolymer coating is applied. Over the terpolymer a polymer cap coat is applied. The cap coat may optionally serve as a diffusion barrier to further control the drug release, or provide a separate drug. The cap coat may be merely a biocompatible polymer applied to the surface of the sent to protect the stent and have no effect on elusion rates.

The following non-limiting examples illustrate some of the various aspects of compositions and methods used to provide implantable medical devices with controlled release coatings. Various polymer compositions were prepared and analyzed in accordance with the teachings of the present invention. The present inventors have determined that the drug release rates and profiles are optimum if the polymer's total solubility parameter ($\delta_T$) is approximately equal to a bioactive agent's solubility parameter ($\delta$). For the purposes of the present invention the polymer's total solubility parameter ($\delta_T$) is considered approximately equal to a bioactive agent's solubility parameter ($\delta$) if their respective $\delta$ values fall with in plus or minus 10 $J^{1/2}/cm^{3/2}$, and/or the difference between at least one solubility parameter of each of the at least two polymers is no greater than about 5 $J^{1/2}/cm^{3/2}$.

Furthermore, in one embodiment of the present invention compatible polymer blends are made wherein the ratio of low Tg polymer to high Tg polymer is in the range of 20:80 to 80:20. In one particular embodiment the ratio of low Tg polymer to high Tg polymer is 50:50. In another embodiment the ratio of low Tg polymer to high Tg polymer is 60:40. In another embodiment the ratio of low Tg polymer to high Tg polymer is 70:30 In another embodiment the ratio of low Tg polymer to high Tg polymer is 80:20. It is understood that these ratios and ranges are approximate and that the exact ratio of low Tg polymer to high Tg polymer is determined in accordance with the present teachings.

For exemplary purposes three anti-restenotic, bioactive compositions were used to test the controlled release kinetics of the present invention. The solubility parameter for each drug is 17.5 $\delta$. The drugs were given the laboratory designators A-19 (rapamycin), A-20 (evrolimus) and A-24. A-24, aka ABT-578, was assigned to a tetrazole-containing macrolide antibiotic depicted in below as Formula 1 (see also U.S. Pat. No. 6,015,815, filed Sep. 24, 1998 and U.S. Pat. No. 6,329,386, filed Nov. 11, 1999 both of which are hereby incorporated in their entirety). For ease of reference, the compound depicted below in Formula 1 will be referred to herein, and in the claims, as ABT-578.

Formula 1

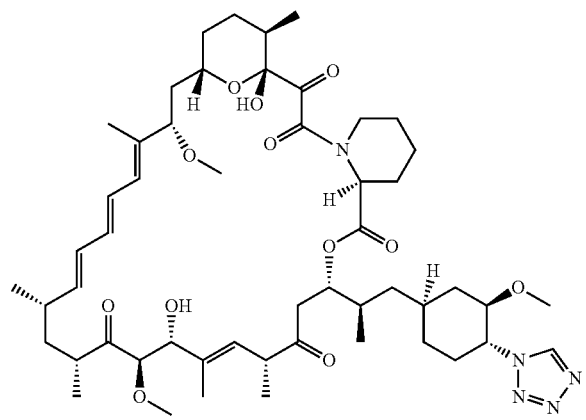

1,18-Dihydroxy-19,30-dimethoxy-12-[2-(3-methoxy-4-methyl-cyclohexyl)-1-methyl-ethyl]-15,17,21,23,29,35-hexamethyl-11,36-dioxa-4-aza-tricyclo[30.3.1.0$^{4,9}$]hexatriaconta-16,24,26,28-tetraene-2,3,10,14,20-pentaone; compound with 1H-tetrazole Table I lists the copolymers used in the following exemplary embodiments. These polymers were prepared using methods known to those skilled in the art of polymer chemistry and as detailed in references such as, A. Ravve. Principles of Polymer Chemistry, Second Edition. 2000. Kluwer Academic/Plenum Publishers, New York. ISBN 0-306-46368-7; H. Allcock and F. Lampe. Contemporary Polymer Chemistry. 1981. Prentice-Hall, New Jersey. ISBN 0-13-170258-0. and A. Tonelli. Polymers from the Inside Out. 2001. Wiley-Interscience. ISBN 0-471-38138-1. All of these references are incorporated by reference herein; additional exemplary teachings are also provided.

The following abbreviations will be used in referring to the various exemplary polymer compositions: VAc=vinyl acetate monomer; BMA=butyl methacrylate monomer; HMA=hexyl methacrylate monomer; LMA=lauryl methacrylate monomer; NVP=N-vinyl pyrrolidone monomer and PEVc=(poly)ethylene-vinyl acetate copolymer.

TABLE 1

COPOLYMER AND TERPOLYMER COMPOSITIONS

| Polymer Composition | mole % of each monomer | Polymer ID | δ | Tg (° C.) |
|---|---|---|---|---|
| VAc:nBMA | 5/95 | A | 18.0 | 20.6 |
| VAc:nBMA | 10/90 | B | 18.1 | 21.0 |
| VAc:nBMA | 70/30 | C | 19.1 | 28 |
| VAc:nHMA:NVP | 7-30/40-75/19-30 | D | | |
| VAc:nHMA:NVP | 30/40/30 | D1 | 21.0 | 21.0 |
| VAc:nHMA:NVP | 20/60/20 | D2 | 17.8 | 12.2 |
| VAc:nHMA:NVP | 10/70/20 | D3 | 17.9 | 8.6 |
| VAc:nHMA:NVP | 9/71/20 | D4 | 17.9 | 8.2 |
| VAc:nHMA:NVP | 7/73/20 | D5 | 18.0 | 7.5 |
| VAc:nHMA:NVP | 7/74/19 | D6 | 18.0 | 7.0 |
| VAc:nLMA:NVP | 30/40/30 | E | 21.0 | −11 |

Table 2 represents the exemplary polymer blend prepared in accordance with the teachings of the preset invention and the resulting $\delta_T$ value for each polymer blend. The blends were prepared such that the resulting $\delta_T$ fell between 15 and 21 δ to be compatible with drugs' δ of 17.5.

TABLE 2

EXEMPLARY COMPATIBILIZED CONTROLLED RELEASE COATINGS

| Compatibilized Polymer Blend | Weight percent of polymers[1] | Polymer Blend ID | $\delta_T$ |
|---|---|---|---|
| PEVAc:Polymer A | 50/50 | I | 17.7 |
| PEVAc:Polymer A | 60/40 | II | 17.8 |
| PEVAc:Polymer B | 50/50 | III | 17.8 |
| PEVAc:Polymer B | 40/60 | IV | 17.8 |
| PEVAc:Polymer B:Polymer C | 40/50/10 | V | 17.9 |
| PEVAc:Polymer B:Polymer C | 40/40/20 | VI | 18.0 |
| PEVAc:Polymer B:Polymer C | 50/41.7/8.3 | VII | 17.8 |
| PEVAc:Polymer B:Polymer C | 50/33.3/16.7 | VIII | 17.9 |
| PEVAc:Polymer B:Polymer C | 60/33.3/6.7 | IX | 17.8 |
| PEVAc:Polymer B:Polymer C | 60/26.7/13.3 | X | 17.8 |
| PEVAc:Polymer E | 20/80 | XI | 20.2 |
| Polymer B:Polymer D1 | 80/20 | XII | 18.0 |
| Polymer B:Polymer D1 | 70/30 | XIII | 18.0 |
| Polymer B:Polymer D1 | 60/40 | XIV | 18.0 |
| Polymer B:Polymer D1 | 50/50 | XV | 18.0 |
| Polymer B:Polymer D1 | 40/60 | XVI | 18.0 |

[1]The percent polymer component is measured on a weight-percent basis.

EXAMPLE 1 A

General Method of the Two-Step Synthesis of Segmented n-Butyl Methacrylate and Vinyl Acetate Copolymers One embodiment of the present invention is exhibited by a two-step synthesis of a copolymer with n-butyl methacrylate and vinyl acetate segments. In the first step of the synthesis, predetermined amounts of n-butyl methacrylate (BMA) and vinyl acetate (VAc) were mixed in a pre-dried glass reactor equipped for mechanical stirring while providing a nitrogen environment on the reactants. The mixture was then sparged with nitrogen for about five minutes. A requisite amount of azo-bis-butyronitrile (Azo) was added to the mixture. In most cases, isopropyl alcohol (IPA) sparged with nitrogen was also added to the mixture. The mixture was heated to the desired temperature under nitrogen and stirred for a certain period of time until the commencement of the second step.

In the second step of the synthesis, a second aliquot of the Azo free radical initiator and IPA were added prior to introduction of a second charge of monomer or comonomer. The monomer and comonomer were also sparged with nitrogen. The polymerization was continued at the desired temperature until monomer consumption practically ceased, maintaining agitation while possible.

At the conclusion of the second step, the heating was stopped and the product was mixed in the reactor with a suitable solvent such as acetone to facilitate the polymer purification by precipitation in a cold non-solvent such as water or methanol or a mixture thereof. The precipitated copolymer was then isolated by filtration and allowed to dry in a laminar flow hood under reduced pressure at room temperature until a constant dry weight was achieved. Further drying can be accomplished by heating under reduced pressure until a constant dry weight is achieved.

EXAMPLE 1B

General Methods of Analysis

A set of general analysis methods was used to monitor and characterize the polymerization reactions. In-process monitoring of the polymerization reaction was achieved by the analysis of residual monomers and molecular weight build-up using gel permeation chromatography (GPC) with dichloromethane as a solvent.

The purified copolymer was characterized with infrared analysis using a film prepared from a chloroform solution. The composition of the purified copolymer was determined with nuclear magnetic resonance (NMR), using $CDCL_3$ as a solvent. Number average (Mn) and weight average ($M_W$) molecular weights were measured using GPC with dichloromethane (DCM) or tetrahydrofuran (THF) as a solvent, and the inherent viscosity (I.V.) with chloroform.

EXAMPLE 1C

General Method of Film Formation and Determination of Percent Elongation

Fracture strain characteristics of the polymeric material may be measured by forming the polymer into a sheet, and applying strain to a sample of the material, and determining when the sample breaks, thereby determining the fracture strain.

The dried polymer was compression-molded into a film about 0.1 mm thick using a heated laboratory Carver press. The temperature, pressure, and time used varied with the copolymer composition—typically above 50° C., 3,000 lbs, and 2 minutes, respectively. The pressed polymer was then quick-quenched to about 25° C. and removed. The molded film was cut into 13×40 mm pieces. The percent elongation was determined on a Mini-Bionix Universal Tester using a gauge length of 19 mm and strain rate of 0.5 mm/s.

EXAMPLES 2A-2J

Two-Step Synthesis of VAc and BMA Segmented Chain Copolymer with BMA in the Second Step A segmented chain copolymer was synthesized in a two-step procedure using only BMA in the second step. Reaction charge and conditions for the preparation of ten copolymers are summarized in Table 3A and Table 3B. The copolymers were made using a (1) high VAc to BMA ratio and only BMA in the second step; (2) polymerization temperature of 55° C. to 70° C.; and (3) no or variable amounts of IPA.

TABLE 3A

TWO-STEP SYNTHESIS AND PROPERTIES OF SEGMENTED VAc TO BMA COPOLYMERS USING ONLY BMA IN THE SECOND STEP

| | Example Number | | | | |
|---|---|---|---|---|---|
| | 2A | 2B | 2C | 2D | 2E |
| Step 1 | | | | | |
| VAc/BMA (g/g) | 8/2 | 23/6 | 94/100 | 90/10 | 80/20 |
| Azo (mg) | 38 | 100 | 249 | 249 | 300 |
| IPA (mL) | 0 | 0 | 100 | 10 | 10 |
| R Time (hour)/Temp (° C.) | 1/70 | 1/70 | 20/60 | 23/60 | 53/55 |
| Step 2 | | | | | |
| BMA/VAc (g/g) | 8/0 | 22/0 | 100/0 | 100/0 | 100/0 |
| Azo (mg) | 0 | 0 | 101 | 101 | 80 |
| IPA (mL) | 0 | 0 | 100 | 100 | 100 |
| R Time (hour)/Temp (° C.) | 35/70 | 35/70 | 26/60 | 21/60 | 37/60 |
| Polymer Properties I.V. | 1.04 | 1.44 | 0.6 | 1.24 | 0.75 |
| $M_w$ (kDa)[1] | >377[2] | 258 | 163 | 395 | 222 |
| Elongation (%) | >250 | >250 | >250 | >250 | >250 |

[1]In DCM or otherwise as indicated.
[2]In THF.

TABLE 3B

TWO-STEP SYNTHESIS AND PROPERTIES OF SEGMENTED VAc AND BMA COPOLYMERS USING ONLY BMA IN THE SECOND STEP

| | Example Number | | | | |
|---|---|---|---|---|---|
| | 2F | 2G | 2H | 2I | 2J |
| Step 1 | | | | | |
| VAc/BMA (g/g) | 25/8 | 20/8 | 18/10 | 70/10 | 70/10 |
| Azo (mg) | 105 | 100 | 105 | 250 | 250 |
| IPA (mL) | 0 | 0 | 0 | 10 | 10 |
| R Time (hour)/Temp (° C.) | 1/70 | 1/70 | 1/70 | 54/60 | 46/60 |
| Step 2 | | | | | |
| BMA/VAc (g/g) | 22/0 | 20/0 | 22/0 | 120/0 | 120/0 |
| Azo (mg) | 0 | 0 | 0 | 80 | 80 |
| IPA (mL) | 0 | 0 | 0 | 12 | 20 |
| R Time (hour)/Temp (° C.) | 35/70 | 35/70 | 35/70 | 30/60 | 23/60 |
| Polymer Properties I.V. | 1.66 | 1.39 | 1.63 | 0.81 | 0.74 |
| $M_w$ (kDa)[1] | 273 | 268 | 275 | 225 | 264 |
| Elongation (%) | >250 | >250 | >250 | >250 | >250 |

[1]In DCM.

EXAMPLES 3A AND 3B

Two-Step Synthesis of Segmented Polymers of Ethyl Methacrylate with Two Other Comonomers A segmented copolymer was synthesized in a two-step process using ethyl methacrylate (EMA) and two other comonomers. Reaction charge and conditions for the bulk preparation (no IPA was used) of a segmented copolymer of EMA with VAc and BMA are summarized in Table 4 for Example 3A. No IPA was used in the preparation. Example 3B is also described in Table 4. It is based on EMA, ethoxyethyl methacrylate (ETOEMA) and BMA. The properties of the polymers in Examples 3A and 3B are also outlined in Table 4.

TABLE 4

TWO-STEP SYNTHESIS AND PROPERTIES OF SEGMENTED POLYMERS OF ETHYL METHACRYLATE (EMA) WITH TWO OTHER COMONOMERS

| | Example Number | |
|---|---|---|
| | 3A | 3B |
| Step 1 | | |
| VAc/EMA (g/g) | 20/15 | 20/7.5 |
| Added Monomers (g) | VAc/EMA | ETOEMA/EMA |
| Azo (mg) | 100 | 100 |
| R Time (hour)/Temp (° C.) | 2.5/70 | 0.7/70 |
| Step 2 | 7.5 | 22.5 |
| Added Monomer (g) | BMA | BMA |
| R Time (hour)/Temp (° C.) | 34/70 | 2/70 |
| Polymer Properties I.V. | 1.84 | 1.57 |
| $M_w$ (kDa)* | — | — |
| Elongation (%) | >250 | >250 |

*In DCM.

EXAMPLES 4A-4E

Synthesis of Segmented BMA and VAc Copolymers with at Least 90:10 BMA to VAc Comonomer Ratio A segmented BMA-VAc copolymer with a BMA to VAc comonomer ratio of at least 90:10 was synthesized. A two-step synthetic scheme was used to prepare the copolymer of Example 4A and entailed 1) a brief first step of one copolymerization cycle associated with incomplete consumption of the comonomer; and 2) the addition of a second aliquot of Azo initiator at the beginning of the second copolymerization step. In Example 4B, the copolymerization was conducted in an extended single step using a high single dose of the Azo initiator. The synthesis of Examples 4C and 4D polymers entailed preparing a low molecular prepolymer of one type in the first step and adding a monomer mixture that was rich in BMA in the second step. In Example 4E, a slightly higher temperature was used in the second step. Reaction charges for the preparation of the copolymers of Examples 4A to 4E and their properties are summarized in Table 5.

TABLE 5

SYNTHESIS AND PROPERTIES OF BMA AND VAc SEGMENTED COPOLYMERS WITH AT LEAST 90:10 BMA:VAc COMONOMER RATIO

| | Example Number | | | | |
|---|---|---|---|---|---|
| | 4A | 4B | 4C | 4D | 4E |
| Step 1 | | | | | |
| VAc/BMA (g/g) | 10.5/200 | 20/180 | 15/0 | 0/195 | 15/0 |
| Azo (mg) | 250 | 300 | 200 | 200 | 200 |
| IPA (mL) | 100 | 100 | 100 | 150 | 100 |
| R Time (hr)/Temp (° C.) | 10/65 | 21/65 | 16/65 | 12/65 | 16/65 |

TABLE 5-continued

SYNTHESIS AND PROPERTIES OF BMA AND
VAc SEGMENTED COPOLYMERS WITH AT
LEAST 90:10 BMA:VAc COMONOMER RATIO

| | Example Number | | | | |
|---|---|---|---|---|---|
| | 4A | 4B | 4C | 4D | 4E |
| Step 2 | | | | | |
| BMA/VAc (g/g) | 0/0 | 0/0 | 5/180 | 10.5/5 | 5/180 |
| Azo (mg) | 50 | 50 | 150 | 200 | 150 |
| R Time (hr)/Temp (° C.) | 7/65 | 7/65 | 12/65 | 16/65 | 12/70 |
| Polymer Properties I.V. | 1.08 | — | — | — | — |
| $M_w$ (kDa)* | 314 | 183 | 260 | 300 | 310 |
| Elongation (%) | >250 | >250 | >250 | >250 | >250 |

*In DCM.

EXAMPLES 5A-5D

Synthesis of Segmented VAc and BMA Copolymers with at Least 90:10 VAc:BMA Comonomer Ratio A segmented VAc and BMA copolymer with greater than 90:10 VAc to BMA comonomer ratio was synthesized in a two-step process. The two-step synthesis schemes outlined in Table 6 were used to prepare the copolymers of Examples 5A and 5B. These entailed 1) charging all reactants at the first step; 2) using a relatively higher Azo concentration than those used in the previous examples; 3) extending the reaction time in the first step; and 4) limiting the reaction temperature in the second step to 25° C. For the copolymers of Examples 5C and 5D as in Table 6, the BMA was charged at both steps and an additional amount of IPA was used in the second step.

TABLE 6

SYNTHESIS AND PROPERTIES OF VAc AND BMA
SEGMENTED COPOLYMERS WITH AT LEAST 90:10
VAc:BMA COMONOMER RATIO

| | Example | | | |
|---|---|---|---|---|
| | 5A | 5B | 5C | 5D |
| VAc/BMA (g/g) | 190/10 | 180/20 | 180/10 | 180/15 |
| Azo (mg) | 300 | 300 | 300 | 300 |
| IPA (mL) | 100 | 100 | 100 | 100 |
| R time (hour)/Temp (° C.) | 30/65 | 30/65 | 30/65 | 30/65 |
| Step 2 | | | | |
| BMA/VAc (g/g) | 0/0 | 0/0 | 0/10 | 0/5 |
| Azo (mg) | 0 | 0 | 0 | 0 |
| IPA (mL) | 0 | 0 | 100 | 100 |
| R time (hour)/Temp (° C.) | 12/25 | 12/25 | 12/65 | 12/65 |
| Polymer Properties I.V. | — | 0.25 | — | — |
| $M_w$ (kDa)* | — | 59 | — | — |
| Elongation (%) | >250 | >250 | >250 | >250 |

*In DCM.

EXAMPLE 6

Synthesis of Segmented VAc and BMA Copolymer with 50:50 VAc:BMA Comonomer Ratio

A segmented VAc and BMA copolymer with approximately 50:50 VAc:BMA comonomer ratio by weight was synthesized in a multi-step process. The multi-step synthetic scheme was used to prepare the 50:50 copolymer following the general experimental protocol as described in Example 1 for VAc and BMA copolymerization with the Azo initiator and IPA as a diluent and reaction medium. In the first step, 85 g of VAc was allowed to copolymerize with 10 g of BMA using 200 mg of the Azo initiator and 75 mL of IPA. The polymerization was conducted at 65° C. for 24 hours. At the conclusion of the first step, a mixture of 5 g VAc, 30 g BMA, 50 mg Azo, and 25 mL IPA was added to the reaction product to proceed with the second step. At this step, the copolymerization was conducted at a temperature at about 65° C. for 6 hours. A similar charge was used in the third step, and the copolymerization was conducted at 65° C. for 16 hours. In the fourth step, the same comonomer, Azo and IPA charge was used, and the copolymerization was conducted at 65° C. for 16 hours. At the conclusion of the fourth step, the copolymer may be isolated, purified, and characterized in the manner as described in Example 1.

EXAMPLE 7

Synthesis of Segmented Interpenetrating VAc and BMA Copolymer with an Overall Comonomer Ratio of 50:50

A segmented copolymer consisting of interpenetrating VAc and BMA sequences with an average comonomer ratio of 50:50 by weight was synthesized. The polymerization was conducted in two steps under the general experimental conditions noted in earlier examples. In the first step, a mixture of 90 g VAc, 10 g BMA, 350 mg Azo, and 100 mL IPA was heated at 65° C. for 24 hours. At the conclusion of the first step, a mixture of 10 g VAc, 90 g MBA and 50 mL IPA was added to the reaction mixture, and heated to 65° C. and held there for 16 hours during the second step. The resulting polymer may be isolated, purified, and characterized as described in previous examples.

EXAMPLE 8

Synthesis of Segmented Interpenetrating VAc, nHMA and NVP Terpolymer with an Overall Monomer Ratio of 30:40:30

A segmented terpolymer consisting of interpenetrating VAc, nHMA and NVP sequences with an average monomer ratio of approximately 30:40:30 by weight was synthesized as follows. However, it is understood that the following synthetic process can be used to synthesize numerous terpolymers have the same monomer constituents by with different monomer ratios merely by differing the relative concentrations of the starting materials in accordance with the teachings of the present invention.

Materials
  a) 1-Vinyl-pyrrolidinone, 99+%, Aldrich catalog # V340-9 (L/N 08229KA), (vacuum distilled before use).
  b) Vinyl acetate, 99+%, Aldrich catalog # V150-3 (L/N 03625DA)
  c) n-Hexyl methacrylate, TCI America catalog # M0503 (L/N GBO1)
  d) 1,4-Dioxane, HPLC grade, 99.9%, Aldrich catalog #27053-9 (L/N 02062DA)
  e) 2,2'-Azobisisobutyronitrile (AIBN), Aldrich catalog #44109-0 (L/N 01313EA)
  f) Hexanes, ACS reagent grade, 98.5%, Aldrich catalog #44349-2 (L/N 07346HA)

g) Methanol, HPLC grade, Aldrich catalog #270474 (L/N 03935LA)

Equipment a) 500 mL Reaction kettle (VWR catlog #36390-020, Clamp VWR catalog #36393-030)
b) Stirring shaft (Chemglass catalog # CG-2079A-02)
c) Stirrer bearing (teflon) (Chemglass catalog # CG-2077-01)
d) Thermocouple (Controls Corp.)
e) HPLC delivery pump (Rabbit-HP HPX)
f) Balance (Meffler PM 4600)
g) Ace thread #7 with N2 inlet (Aceglass catalog #5261-16)

Formulation of Charges

|  | Weight (g) |
|---|---|
| Charge One | |
| Vinyl acetate | 25 |
| 1-Vinyl pyrrolidone | 6.5 |
| n-Hexyl methacrylate | 8.5 |
| 1,4-Dioxane | 50 |
| AIBN | 0.375 |
| Charge Two | |
| 1-Vinyl pyrrolidone | 20.5 |
| Hexyl methacrylate | 40 |
| 1,4-Dioxane | 60 |
| AIBN | 0.45 |

Procedures

1) A 500 mL reaction kettle equipped with a mechanical stirrer (Teflon bearing and glass stirring shaft), a thermocouple adapter with $N_2$ inlet an adapter for Charge Two addition tubing and a condenser capped with $N_2$ reaction bubbler, is charged with Charge One.
2) A 20% excess of Charge Two is prepared and stored in a bottle. The Charge Two bottle is capped with a rubber septum thread with Teflon tubing, which is connected to a HPLC delivery pump. The tubing was filled with Charge Two solution. Charge Two bottle is purged with $N_2$ for 2 minutes.
3) The kettle is purged with $N_2$ at a flow rate of about a bubble/sec while under stirring for 20 minutes at room temperature. The $N_2$ bubbling is reduced just enough to maintain a positive pressure.
4) The reaction kettle is lowered to a preheated water bath (temperature set at about 62° C.). The temperature should reach 60° C. in about 5-10 minutes. The reaction is stirred at 60° C. for 25 minutes before Charge Two is added at a rate of 20.16 g/hour. After 120.95 g of Charge Two is added (6 Hours), stop the HPLC pump and the reaction.
5) The reaction kettle is removed from the water bath and reaction is exposed to air and cooled to room temperature with an ice water bath.

The polymer solution is diluted with 2 L of hexanes and the solution is transferred to a flask. The polymer solution in hexanes is cooled to −60° C. with a dry ice-isopropyl alcohol bath for 30 minutes to precipitate out the polymer. The system is warmed up to 40° C. The top solution is decanted as much as possible. The sticky polymer is redissolved in 2 L of hexanes. If the polymer does not completely dissolve at room temperature, warm it up with a water bath to raise the temperature to 50 C. Add just enough chloroform for the polymer to dissolve completely. The cold temperature precipitation is repeated two more times. The polymer is redissolved in 125 mL chloroform and precipitated in 1500 mL methanol cooled to −60° C. The solvent is decanted and the polymer is pressed and washed with some cold methanol. This precipitation is repeated one mote time. The sticky polymer is dissolved in 250 mL of chloroform and transferred to Teflon lined trays. After most of the chloroform is evaporated inside a hood, the polymer is dried in a vacuum oven set at 45° C. under a vacuum of <1 mm Hg overnight. The transparent polymer film is peeled off the Teflon tray.

EXAMPLE 9

Synthesis of Segmented 94:5 VAc:BMA Copolymer Grafted with Short 1:20 VAc:BMA Chains, for an Overall Comonomer Ratio of 95:25 VAc:BMA A segmented copolymer consisting of a 94:5 VAc:BMA copolymer grafted with short 1:20 VAc:BMA chains was synthesized in accordance with another embodiment of the present invention, to form a grafted copolymer with an overall comonomer ratio of 95:25. The polymerization was conducted in two steps, under the usual experimental conditions noted in earlier examples. In the first step, a mixture of 94 g VAc, 5 g BMA, 250 mg Azo, and 100 mL IPA was heated at 65° C. for 24 hours. At the conclusion of this period, 100 mL of IPA were added to the reaction product. This was followed by adding 50 mg of Azo and continuing the heating at 65° C. for 5 minutes prior to adding a mixture of 1 g VAc and 20 g BMA, and then proceeding with the second step of the copolymerization at 65° C. for 12 hours. The resulting polymer may be isolated, purified, and characterized as described in previous examples.

EXAMPLE 10

Preparation of Poly(n-Butyl Methacrylate)

In another embodiment of the current invention, a segmented copolymer was prepared with poly(n-butyl methacrylate). This entailed the use of 200 g BMA, 408 mg Azo initiator, and 150 mL IPA. The polymerization was conducted at 65° C. for 18 hours. The resulting polymer was isolated, purified, and characterized in the usual manner (see Example 1). The polymer was shown to have an I.V. of 0.82 dL/g, $M_w$ (DCM) of 263 kiloDalton (kDa), and its film did not break at over 300% elongation.

Solubility Parameter ($\delta$ and $\delta_T$) Determinations

The solubility parameters of the polymers, compatibilized polymer blends and the bioactive agents used in the present invention were calculated using methods known to those having ordinary skill in the art. For example, see van Krevelen at pages 189 through 226. Specifically see pages 211 through 219. Generally, and not intended as a limitation, there are two accepted methods for calculating solubility: the Hoftyzer-van Kreveln method and the Hoy method. (See for examples: Hoftyzer, P. J. and van Krevelen, D. W. 1976 Properties of Polymers, 2d Edition, Chapter 7, pp 152-155) and Hoy (Hoy, K. L. 1970. J. Paint Techn. 42:76; Tables of Solubility Parameters. Solvent and Coatings. Materials Research and Development Department, Union Carbide Corporation. 1985. and J. Coated Fabrics 1989. 19:53). The results obtained using the algorithmic methods of Hoftyzer-van Krevelen and Hoy are usually within 10% of each other. Therefore, in many cases calculating the solubility parameters for a polymer or other organic compound using both methods and then averaging the results is preferred. However, experimental methods of determining polymer solubility may be used as well.

Preparation of Compatible Controlled Release Coatings

I. Preparation of Stock Solutions

Stock solutions were prepared containing 1% (wt/wt %) of polymer composition or drug dissolved in chloroform according to Table 7.

TABLE 7

PREPARATION OF STOCK SOLUTIONS

| Polymer or Drug Composition | Weight of Polymer or Drug | Volume of Chloroform (sp gr 1.492) |
|---|---|---|
| PEVAc | 0.4659 g | 30.9 mL |
| Polymer A | 0.1421 g | 9.4 mL |
| Polymer B | 0.4233 g | 28.1 mL |
| Polymer C | 0.4432 | 29.4 mL |
| Drug rapamycin | 0.2936 g | 19.5 mL |
| Drug evrolimus | 0.0925 g | 6.1 mL |

II. Preparation of Compatibilized Coating Solutions

Five mL volumes of compatibilized coating solutions were prepared by blending predetermined amounts of stock solutions defined in Table 8 in accordance to the following ratios.

TABLE 8

PREPARATION OF COMPATIBILIZED COATING COMPOSITIONS

| Coating ID | Volume of Drug | Volume of PEVc | Volume and Polymer-Copolymer Composition |
|---|---|---|---|
| I | evrolimus 1.25 mL | 1.875 mL | Copolymer A 1.875 mL |
| II | evrolimus 1.25 mL | 1.5 mL | Copolymer A 2.25 mL |
| III | rapamycin 1.25 ml | 1.875 ml | Copolymer B 1.875 mL |
| IV | rapamycin 1.25 mL | 1.5 mL | Copolymer B 2.25 mL |
| V | rapamycin 1.25 ml | 1.5 mL | Copolymer B 1.875 mL Copolymer C 0.375 mL |
| VI | rapamycin 1.25 mL | 1.5 mL | Copolymer B 1.5 mL Copolymer C 0.75 mL |
| VII | rapamycin 1.25 mL | 1.875 mL | Copolymer B 1.56 mL Copolymer C 0.31 mL |
| VIII | rapamycin 1.25 mL | 1.875 mL | Copolymer B 1.25 mL Copolymer C 0.625 mL |
| IX | rapamycin 1.25 mL | 2.25 mL | Copolymer B 1.25 mL Copolymer C 0.25 mL |
| X | rapamycin 1.25 mL | 2.25 mL | Copolymer B 1.00 mL Copolymer C 0.50 mL |

Application Process

As previously discussed, the compatibilized coating solutions of the present invention can be applied to virtually any medical device surface using standard coating techniques including spraying, dipping, or painting. In one embodiment of the present invention the compatibilized coatings are sprayed onto the surface of a vascular stent that has been previously provided with a parylene C primer coat. The parylene C having been applied first to the cleaned, bare stent surface using vacuum deposition.

Spraying was carried out in an isolator employing an ultrasonic spray device. The spray device's coating chamber was filled with the compatibilized coating solution of the present invention and programmed to deliver approximately 45 µg per mm of stent. In one embodiment 400 µg of compatibilized coating was loaded on a 9 mm stent. The stents were mounted onto a mandrel and sprayed. After the spraying operation was complete the stent was dried under vacuum at room temperature overnight.

In one embodiment of the present invention a parylene primed stent was provided with a coating comprising the terpolymer composition D in Table 1 containing a bioactive agent and a non-drug containing second barrier coat comprising bipolymer composition B in Table 1.

Testing

Coating Durability

Figure 3:
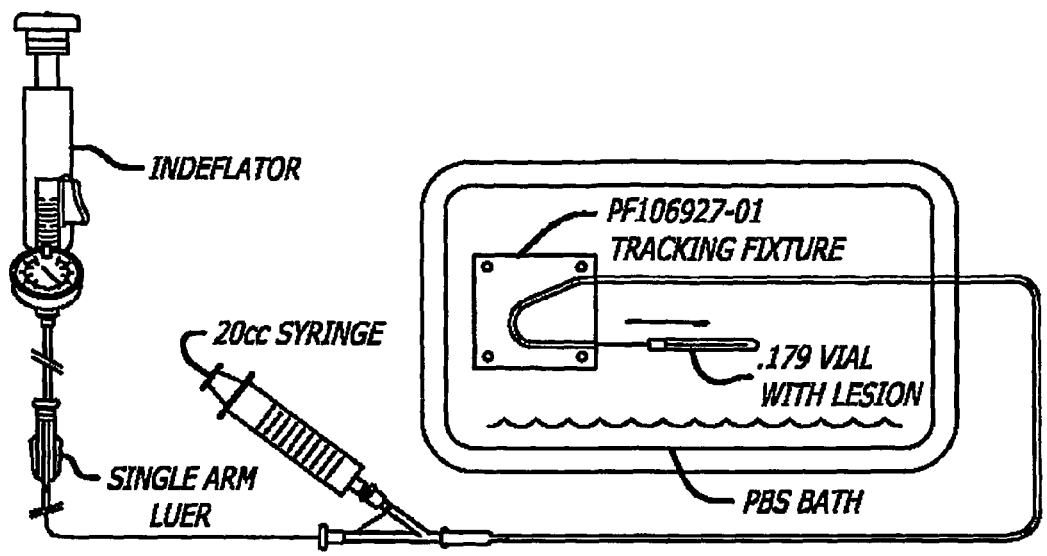
FIG. 3 depicts a tortuous path tubing system used to test coating durability.

The compatibilized control release coatings of the present invention, were tested for durability using a tortuous path tubing system as shown in FIG. 3. Coated stents were mounted on balloon catheters and inserted into the tubing system. The catheter was inserted and removed three times to simulate the wear a stent might endure during insertion and manipulation. Finally the catheter was inflated in a physiological-like environment and the stent coating was examined using high resolution optics and scanning electron microscopy for signs of delamination, cracking and excessive wear.

Drug Elution Profiles

The coated stents were placed in two milliliters of 10 mmole TRIS (pH 6.5) containing 4% sodium dodecyl sulfate (SDS) (TRIS-SDS buffer) and incubated at 37° C. for a total of 38 days. Samples were taken at 1, 2 and 4 hours and again at 24 hours. After the initial 24 hour incubation the stents were placed in fresh TRIS-SDS buffer and incubated for an additional 24 hours at which point they were samples again and then placed in fresh TRIS-SDS buffer. This process was repeated for 30 consecutive days. Samples. Test samples were analyzed for drug concentration using HPLC.

CONCLUSION

Drug eluting polymer coatings for medical devices are becoming increasingly more common. Furthermore, the number of possible polymer-drug combinations is increasing exponentially. Therefore, there is need for reproducible methods of designing drug-polymer compositions such that drug-elution rates/profiles, biocompatibility and structural integrity are compatibilized resulting in optimal coating systems tailored for specific therapeutic functions. The present invention provides both exemplary optimal coating systems and related methods for their reproducible design.

Unless otherwise indicated, all numbers expressing quantities of ingredients, properties such as molecular weight, reaction conditions, and so forth used in the specification and claims are to be understood as being modified in all instances by the term "approximately." Accordingly, unless indicated to the contrary, the numerical parameters set forth in the following specification and attached claims are approximations that may vary depending upon the desired properties sought by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illustrate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A medical device comprising a controlled release coating for an implantable medical device comprising:
a bioactive agent-containing terpolymer-bipolymer blend, wherein the terpolymer-bipolymer blend has a total solubility parameter ($\delta_T$) approximately equal to said bioactive agent's solubility parameter ($\delta$) and wherein $\delta_T$ and $\delta$ is between 15 $J^{1/2}/cm^{3/2}$ to 25 $J^{1/2}/cm^{3/2}$, wherein the terpolymer and bipolymer each include vinyl acetate and an alkyl methacrylate.

2. The medical device according to claim 1 wherein said coating has a glass transition point (Tg) between approximately −20° C. and 50° C.

3. The medical device according to claim 2 wherein said coating has a glass transition point (Tg) between approximately 10° C. and 35° C.

4. The medical device according to claim 1 wherein said terpolymer comprises monomer subunits consisting of vinyl acetate (VAc), alkyl methacrylate (AMA) and n-vinyl pyrrolidone (NVP) and said bipolymer comprises monomer subunits consisting of VAc and AMA.

5. The medical device according to claim 4 wherein said relative mole percent concentrations of said monomer subunits in said terpolymer comprises 7-30% (VAc), 40-75% (AMA) and 19-30% (NVP).

6. The medical device according to claim 4 wherein said relative mole percent concentrations of said monomer subunits in said bipolymer comprises 5-70% VAc and 30-95% AMA.

7. The medical device according to claim 4 wherein said alkyl of said alkyl methacrylate is selected from the group consisting of methyl, ethyl, propyl, butyl, pentyl, and hexyl methacrylate.

8. The medical device according to claim 1 wherein said $\delta_T$ is approximately 15 to 21 and said polymer blend comprises from 25% to 80% bipolymer and from 20% to 75% terpolymer.

9. The medical device according to claim 1 wherein said terpolymer has a lower Tg than said bipolymer.

10. The medical device according to claim 1 wherein said bioactive agent is selected from the group consisting of anti-proliferatives including, but not limited to, macrolide antibiotics, FKBP 12 binding compounds, estrogens, chaperone inhibitors, protease inhibitors, protein-tyrosine kinase inhibitors, peroxisome proliferator-activated receptor gamma ligands (PPARγ), hypothemycin, nitric oxide, bisphosphonates, epidermal growth factor inhibitors, antibodies, antibiotics, proteasome inhibitors anti-sense nucleotides and transforming nucleic acids.

11. The medical device according to claim 10 wherein said antiproliferative is a FKBP 12 binding compound.

12. The medical device according to claim 11 wherein said FKBP 11 binding compound is a macrolide antibiotic.

13. The medical device according to claim 12 wherein said macrolide antibiotic is rapamycin, everolimus, or ABT-578.

14. A vascular stent comprising:
a structure comprising a material, said material having a coating thereon comprised of a hydrophobic polymer;
a bioactive agent-containing terpolymer-bipolymer blend over said hydrophobic polymer wherein the difference between the solubility parameters of said terpolymer-bipolymer blend and said bioactive agent is no greater than 10 $J^{1/2}/cm^{3/2}$ and the total solubility parameter ($\delta_T$)

of said bioactive agent-containing terpolymer-bipolymer blend is no greater than 25 $J^{1/2}/cm^{3/2}$, wherein the terpolymer and bipolymer each include vinyl acetate and an alkyl methacrylate.

15. The vascular stent according to claim 14 wherein said hydrophobic polymer is parylene or a parylene derivative.

16. The vascular stent according to claim 14 wherein said terpolymer comprises monomer subunits consisting of vinyl acetate (VAc), alkyl methacrylate (AMA) and n-vinyl pyrrolidone (NVP) and said bipolymer comprises monomer subunits consisting of VAc and AMA.

17. The vascular stent according to claim 16 wherein said relative mole percent concentrations of said monomer subunits in said terpolymer comprises 7-30% (VAc), 40-75% (AMA) and 19-30% (NVP).

18. The vascular stent according to claim 14 wherein said relative mole percent concentrations of said monomer subunits in said bipolymer comprises 5-70% VAc and 30-95% AMA.

19. The vascular stent according to claim 16 wherein said alkyl of said alkyl methacrylate is selected from the group consisting of methyl, ethyl, propyl, butyl, pentyl, and hexyl methacrylate.

20. The vascular stent according to claim 14 wherein said $\delta_T$ is approximately 15 to 21 and said polymer blend comprises from 25% to 80% bipolymer and from 20% to 75% terpolymer.

21. The vascular stent according to claim 14 wherein said terpolymer has a lower Tg than said bipolymer.

22. The vascular stent according to claim 14 wherein said bioactive agent is selected from the group consisting of anti-proliferatives including, but not limited to, macrolide antibiotics, FKBP 12 binding compounds, estrogens, chaperone inhibitors, protease inhibitors, protein-tyrosine kinase inhibitors, peroxisome proliferator-activated receptor gamma ligands (PPARγ), hypothemycin, nitric oxide, bisphosphonates, epidermal growth factor inhibitors, antibodies, antibiotics, proteasome inhibitors anti-sense nucleotides and transforming nucleic acids.

23. The vascular stent according to claim 22 wherein said antiproliferative is a FKBP 12 binding compound.

24. The vascular stent according to claim 23 wherein said FKBP 12 binding compound is a macrolide antibiotic.

25. The vascular stent according to claim 24 wherein said macrolide antibiotic is rapamycin, everolimus, or ABT-578.

26. A vascular stent device comprising a controlled release coating comprising:
a polymer component comprising a terpolymer-bipolymer polymer blend,
wherein
the terpolymer and bipolymer each include vinyl acetate; and
a drug, wherein the $\delta_T$ for the drug is within ±10 $J^{1/2}/cm^{3/2}$ of the total solubility parameter $\delta_T$ for the polymer component.

27. An implantable medical device comprising a controlled release, non-bioerodable coating comprising:
a terpolymer-bipolymer blend, wherein the terpolymer-bipolymer blend has a total solubility parameter ($\delta_T$) approximately equal to a bioactive agent's solubility parameter ($\delta$) and wherein $\delta_T$ and $\delta$ is between 15 $J^{1/2}/cm^{3/2}$.

28. The medical device according to claim 27 wherein said coating has a glass transition point (Tg) between approximately −20° C. and 50° C.

29. The medical device according to claim 28 wherein said coating has a glass transition point (Tg) between approximately 10° C. and 35° C.

30. The medical device according to claim 27 wherein said $\delta_T$ is approximately 15 to 21 and said polymer blend comprises from 25% to 80% bipolymer and from 20% to 75% terpolymer.

31. The medical device according to claim 27 wherein said terpolymer has a lower Tg than said bipolymer.

32. The medical device according to claim 27 wherein said bioactive agent is selected from the group consisting of anti-proliferatives including, but not limited to, macrolide antibiotics, FKBP 12 binding compounds, estrogens, chaperone inhibitors, protease inhibitors, protein-tyrosine kinase inhibitors, peroxisome proliferator-activated receptor gamma ligands (PPARγ), hypothemycin, nitric oxide, bisphosphonates, epidermal growth factor inhibitors, antibodies, antibiotics, proteasome inhibitors anti-sense nucleotides and transforming nucleic acids.

33. The medical device according to claim 32 wherein said antiproliferative is a FKBP 12 binding compound.

34. The medical device according to claim 33 wherein said FKBP 12 binding compound is a macrolide antibiotic.

35. The medical device according to claim 34 wherein said macrolide antibiotic is rapamycin, everolimus, or ABT-578.

36. An implantable medical device comprising a controlled release coating comprising:
a terpolymer-bipolymer blend, wherein the terpolymer-bipolymer blend has a total solubility ($\delta_T$) approximately equal to a bioactive agent's solubility parameter ($\delta$) and wherein $\delta_T$ and $\delta$ is between 15 $J^{1/2}/cm^{3/2}$ to 25 $J^{1/2}/cm^{3/2}$;
wherein said terpolymer comprises monomer subunits consisting of vinyl acetate (VAc), alkyl methacrylate (AMA) and n-vinyl pyrrolidone (NVP) and said bipolymer comprises monomer subunits consisting of VAc and AMA.

37. The medical device according to claim 36 wherein said relative mole percent concentrations of said monomer subunits in said terpolymer comprises 7-30% (VAc), 40-75% (AMA) and 19-30% (NVP).

38. The medical device according to claim 36 wherein said relative mole percent concentrations of said monomer subunits in said bipolymer comprises 5-70% VAc and 30-95% AMA.

39. The medical device according to claim 36 wherein said alkyl of said alkyl methacrylate is selected from the group consisting of methyl, ethyl, propyl, butyl, pentyl, and hexyl methacrylate.

40. A vascular stent comprising:
a structure comprising a material, said material having a hydrophobic polymer disposed thereon;
a controlled release, non-bioerodable coating over said hydrophobic polymer wherein said controlled release, non-bioerodable coating comprises a bioactive agent-containing terpolymer-bipolymer blend wherein the difference between the solubility parameters of said terpolymer-bipolymer blend and said bioactive agent is no greater than 10 $J^{1/2}/cm^{3/2}$ and the total solubility parameter ($\delta_T$) of said bioactive agent-containing terpolymer-bipolymer blend is no greater than 25 $J^{1/2}/cm^{3/2}$.

41. The vascular stent according to claim 40 wherein said hydrophobic polymer is parylene or a parylene derivative.

42. The vascular stent according to claim 40 wherein said $\delta_T$ is approximately 15 to 21 and said polymer blend comprises from 25% to 80% bipolymer and from 20% to 75% terpolymer.

43. The vascular stent according to claim 40 wherein said terpolymer has a lower Tg than said bipolymer.

44. The vascular stent according to claim 40 wherein said bioactive agent is selected from the group consisting of anti-proliferatives including, but not limited to, macrolide antibiotics, FKBP 12 binding compounds, estrogens, chaperone inhibitors, protease inhibitors, protein-tyrosine kinase inhibitors, peroxisome proliferator-activated receptor gamma ligands (PPARγ), hypothemycin, nitric oxide, bisphosphonates, epidermal growth factor inhibitors, antibodies, antibiotics, proteasome inhibitors anti-sense nucleotides and transforming nucleic acids.

45. The vascular stent according to claim 44 wherein said antiproliferative is a FKBP 12 binding compound.

46. The vascular stent according to claim 45 wherein said FKBP 12 binding compound is a macrolide antibiotic.

47. The vascular stent according to claim 46 wherein said macrolide antibiotic is rapamycin, everolimus, or ABT-578.

48. A vascular stent comprising:
a structure comprising a material, said material having a hydrophobic polymer disposed thereon;
a controlled release, non-bioerodable coating over said hydrophobic polymer wherein said controlled release, non-bioerodable coating comprises a bioactive agent-containing terpolymer-bipolymer blend wherein the difference between the solubility parameters of said terpolymer-bipolymer blend and said bioactive agent is no greater than 10 $J^{1/2}/cm^{3/2}$ and the total solubility parameter ($\delta_T$) of said bioactive agent-containing terpolymer-bipolymer blend is no greater than 25 $J^{1/2}/cm^{3/2}$;
wherein said terpolymer comprises monomer subunits consisting of vinyl acetate (VAc), alkyl methacrylate (AMA) and n-vinyl pyrrolidone (NVP) and said bipolymer comprises monomer subunits consisting of VAc and AMA.

49. The vascular stent according to claim 48 wherein said relative mole percent concentrations of said monomer subunits in said terpolymer comprises 7-30% (VAc), 40-75% (AMA) and 19-30% (NVP).

50. The vascular stent according to claim 48 wherein said relative mole percent concentrations of said monomer subunits in said bipolymer comprises 5-70% VAc and 30-95% AMA.

51. The vascular stent according to claim 50 wherein said alkyl of said alkyl methacrylate is selected from the group consisting of methyl, ethyl, propyl, butyl, pentyl, and hexyl methacrylate.

\* \* \* \* \*